(12) United States Patent
Chan et al.

(10) Patent No.: US 7,674,954 B2
(45) Date of Patent: Mar. 9, 2010

(54) **DNA CONSTRUCTS THAT CONTAIN *HELIANTHUS ANNUUS* HAHB-10 GENE CODING SEQUENCE, METHOD FOR GENERATING PLANTS WITH A SHORTENED LIFE CYCLE AND A HIGH TOLERANCE TO HERBICIDAL COMPOUNDS AND TRANSGENIC PLANTS WITH THAT SEQUENCE**

(75) Inventors: Raquel Lia Chan, Santa Fe (AR); Daniel H. Gonzalez, Santa Fe (AR); Carlos A. Dezar, Santa Fe (AR); Eva C. Rueda, Santa Fe (AR)

(73) Assignees: Universidad Nacional del Litoral, Santa Fe (AR); Consejo Nacional de Investigaciones Cientificas Y Technicas, Buenos Aires (AR); Bioceres, S.A., Rosario (AR)

( * ) Notice: Subject to any disclaimer, the term of this patent is extended or adjusted under 35 U.S.C. 154(b) by 518 days.

(21) Appl. No.: 11/543,992

(22) Filed: Oct. 6, 2006

(65) Prior Publication Data

US 2007/0234439 A1 Oct. 4, 2007

(30) Foreign Application Priority Data

Mar. 29, 2006 (AR) .............................. P060101207

(51) Int. Cl.
*C12N 15/82* (2006.01)
(52) U.S. Cl. .................................................... 800/290
(58) Field of Classification Search ....................... None
See application file for complete search history.

(56) References Cited

OTHER PUBLICATIONS

Gonzalez D.H. et al. Interaction between proteins containing homeodomains associated to leucine zippers from sunflower. Biochim Biophys Acta. Mar 20, 1997;1351(1-2):137-49.*
Schena M. et al. The HAT4 gene of *Arabidopsis* encodes a developmental regulator. Genes Dev. Mar. 1993;7(3):367-79.*
Bagnall, D.J., et al., "Flowering Responses to Altered Expression of Phytochrome in Mutants and Transgenic Lines of *Arabidopsis thaliana* (L.) Heynh," *Plant Physiol.* 108:1495-1503, American Society of Plant Physiologists (1995).
Boccalandro, H.E., et al., "Increased Phytochrome B Alleviates Density Effects on Tuber Yield of Field Potato Crops," *Plant Physiol.* 133:1539-1546, American Society of Plant Biologists (2003).
Carabelli, M., et al., "Twilight-zone and canopy shade induction of the *Athb-2* homeobox gene in green plants," *Proc. Natl. Acad. Sci. USA* 93:3530-3535, The National Academy of Sciences of the United States of America (1996).
Carabelli, M., et al., "The *Arabidopsis Athb-2* and -4 genes are strongly induced by far-red-rich light," *Plant J.* 4:469-479, The Society for Experimental Biology (1993).
Casal, J.J., et al., "Signaling for developmental plasticity," *Trends Plant Sci.* 9:309-314, Elsevier Ltd. (2004).

Chan, R.L., et al., "Homeoboxes in plant development," *Biochim. Biophys. Acta* 1442:1-19, Elsevier Science B.V. (1998).
Chan, R.L., et al., "A cDNA Encoding an HD-Zip Protein from Sunflower," *Plant Physiol.* 106:1687-1688, American Society for Plant Physiologists (1994).
Cho, D.-S., et al., "*FIN5* Positively Regulates Far-red Light Responses in *Arabidopsis thaliana*," *Plant Cell Physiol.* 44:565-572, Japanese Society of Plant Physiologists (2003).
Delarue, M., et al., "*Sur2* mutations of *Arabidopsis thaliana* defines a new locus involved in the control of auxin homeostasis," *Plant J.* 14:603-611, Blackwell Science Ltd. (1998).
Deng, X., et al., "Characterization of five novel dehydration-responsive homeodomain leucine zipper genes from the resurrection plant *Craterostigma plantagineum*," *Plant Mol. Biol.* 49:601-610, Kluwer Academic Publishers (2002).
Dezar, C.A., et al., "*Hahb-4*, a sunflower homeobox-leucine zipper gene, is a developmental regulator and confers drought tolerance to *Arabidopsis thaliana* plants," *Transgen. Res.* 14:429-440, Springer (Mar. 2005).
Gehring, W.J., "Homeo Boxes in the Study of Development," *Science* 236:1245-1252, American Association for the Advancement of Science (1987).
Gehring, J.W., et aL., "Homeodomain Proteins," *Annu. Rev. Biochem.* 63:487-526, Annual Reviews Inc. (1994).
Gonzalez, D.H., et al., "Interaction between proteins containing homeodomains associated to leucine zippers from sunflower," *Biochim. Biophys. Acta* 1351:137-149, Elsevier Science B.V. (1997).
Gonzalez, D.H., and Chan, R.L., "Screening cDNA libraries by PCR using λ sequencing primers and degenerate oligonucleotides," *Trends Genet.* 9:231-232, Elsevier Science Publishers Ltd. (1993).
Hanson, J., et al., "Sugar-dependent alterations in cotyledon and leaf development in transgenic plants expressing the HDZhdip gene *ATHB13*," *Plant Mol. Biol.* 45:247-262, Kulwer Academic Publishers (2001).
Himmelbach, A., et al., "Homeodomain protein ATHB6 is a target of the protein phosphatase ABI1 and regulates hormone responses in *Arabidopsis*," *EMBO J.* 21:3029-3038, European Molecular Biology Organization (2002).
Lee, Y.-H., and Chun, J.-Y., "A new homeodomain-leucine zipper gene from *Arabidopis thaliana* induced by water stress and abscisic acid treatment," *Plant Mol. Biol.* 37:377-384, Kluwer Academic Publishers (1998).
Ma, L., et al., "Light Control of *Arabidopsis* Development Entails Coordinated Regulation of Genome Expression and Cellular Pathways," *Plant Cell.* 13:2589-2607, American Society of Plant Biologists (2001).
Mattsson, J., et al., "A new homeobox-leucine zipper gene from *Arabidopsis thaliana*," *Plant Mol. Biol.* 18:1019-1022, Kluwer Academic Publishers (1992).

(Continued)

*Primary Examiner*—Cynthia Collins
(74) *Attorney, Agent, or Firm*—Sterne, Kessler, Goldstein & Fox P.L.L.C.

(57) ABSTRACT

The present invention refers to a gene from *Helianthus annuus* encoding a transcription factor that comprises a homeodomain associated with a leucine zipper. This gene is named Hahb-10. The transcription factor Hahb-10 can be used in DNA constructs to transform host cells and plants. Transgenic plants that overexpress this transcription factor are more tolerant to herbicides, and have a shorter life cycle.

5 Claims, 12 Drawing Sheets

OTHER PUBLICATIONS

Figure 1:
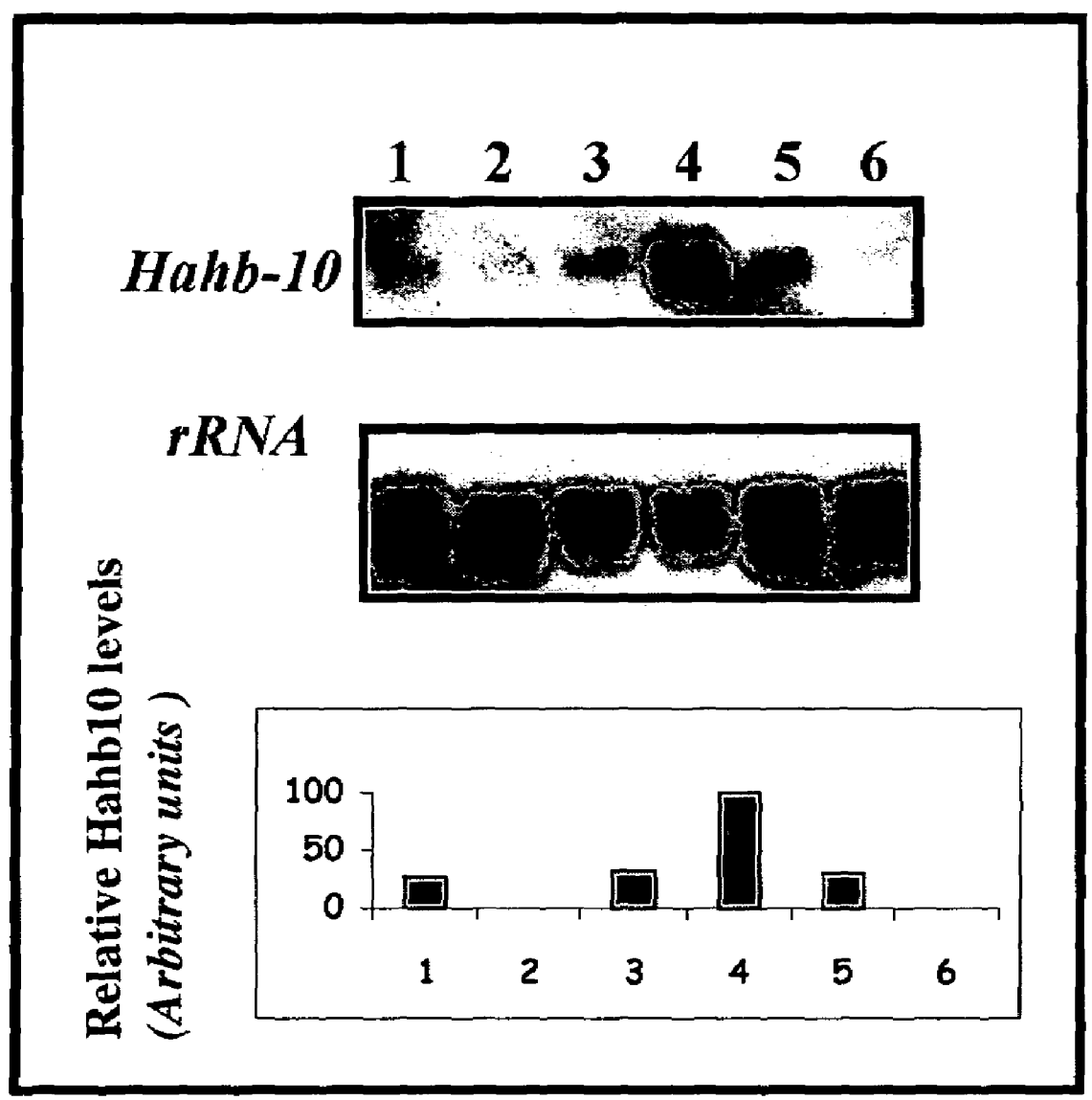

Morelli, G., and Ruberti, I., "Shade Avoidance Responses. Driving Auxin along Lateral Routes," *Plant Physiol.* 122:621-626, American Society of Plant Physiologists (2000).

Morelli, G., and Ruberti, I., "Light and shade in the photocontrol of *Arabidopsis* growth," *Trends Plant Sci.* 7:399-404, Elsevier Science Ltd. (2002).

Ohgishi, M., et al., "Negative autoregulation of the *Arabidopsis* homeobox gene *ATHB-2*," *Plant J.* 25:389-398, Blackwell Science Ltd. (2001).

Palena, C.M., et al., "A monomer-dimer equilibrium modulates the interaction of the sunflower homeodomain leucine-zipper protein Hahb-4 with DNA," *Biochem J.* 341:81-87, Biochemical Society (1999).

Ruberti, I., et al., "A novel class of plant proteins containing a homeodomain with a closely linked leucine zipper motif," *EMBO J.* 10:1787-1791, Oxford University Press (1991).

Sawa, S., et al., "The *HAT2* gene, a member of the HD-Zip gene family, isolated as an auxin inducible gene by DNA microarray screening, affects auxin responses in *Arabidopsis*," *Plant J.* 32:1011-1022, Blackwell Publishing Ltd. (2002).

Schena, M., et al., "The *HAT4* gene of *Arabidopsis* encodes a developmental regulator," *Genes Dev.* 7:367-379, Cold Spring Harbor Laboratory Press (1993).

Schena, M., and Davis, R., "HD-Zip proteins: Members of an *Arabidopsis* homeodomain protein superfamily," *Proc. Natl. Acad. Sci. USA* 89:3894-3898, The National Academy of Sciences of the United States of America (1992).

Sessa, G., et al., "The Athb-1 and -2 HD-Zip domains homodimerize forming complexes of different DNA binding specificities," *EMBO J.* 12:3507-3517, Oxford University Press (1993).

Steindler, C., et al., "Shade avoidance responses are mediated by the ATHB-2 HD-Zip protein, a negative regulator of gene expression," *Development* 126:4235-4245, The Company of Biologists Limited (1999).

Steindler, C., et al., "Phytochrome A, phytochrome B and other phytochrome(s) regulate *ATHB-2* gene expression in etiolated and green *Arabidopsis* plants," *Plant, Cell and Enviorn.* 20:759-763, Blackwell Science Ltd. (1997).

Söderman, E., et al., "The *Arabidopsis* homeobox gene *ATHB-7* is induced by water deficit and by abscisic acid," *Plant J.* 10:375-381, The Society for Experimental Biology (1996).

Söderman, E., et al., "The HD-Zip gene *ATHB6* in *Arabidopsis* is expressed in developing leaves, roots and carpels and up-regulated by water deficit conditions," *Plant Mol. Biol.* 40:1073-1083, Kluwer Academic Publishers (1999).

Söderman, E., et al., "Expression patterns of novel genes encoding homeodomain leucine-zipper proteins in *Arabidopsis thaliana*," *Plant Mol. Biol.* 26:145-154, Kluwer Academic Publishers (1994).

Tron, A.E., et al., "Redox Regulation of Plant Homeodomain Transcription Factors," *J. Biol. Chem.* 277:34800-34807, The American Society for Biochemistry and Molecular Biology, Inc. (2002).

Valle, E.M., et al., "Isolation and expression pattern of *hahr1*, a homeobox-containing cDNA from *Helianthus annuus*," *Gene* 196:61-68, Elsevier Science B.V. (1997).

Wang, Y., et al., "The *Arabdiposis* homeobox gene, *ATHB16*, regulates leaf development and the sensitivity to photoperiod in *Arabidopsis*," *Dev. Biol.* 264:228-239, Elsevier Inc. (2003).

\* cited by examiner

```
  1 taaacatcga tcaatctaca catcttttat tcagatggat tttcatggat ttgccgaaca
 61 tgcactggaa ctacgcctta gtacaacatc atcggtggcc gaaaacacaa cgaatcccat
121 caagaagcct agcccgagtt ctgatcattg tcttgaacca tctctaactt tggctctttc
181 tggtgattca tgcggtggtt cgtcgttctc tatcgctagt gcgaagaggg aaagagaggt
241 tccgagtgaa gaatcggaga gaggaggaga gaacactagt ggtgaagaag atgaagatgg
301 tggtgtgaat ggtaagaaga aactcaggtt aactaaagct caatctggac tattagagga
361 agccttcaaa cttcacacaa ctttaaaccc taaacaaaag caagagcttg caagggactt
421 aaagctaagg cctagacaag ttgaagtatg gttccaaaac aggagagcaa gaacaaaact
481 gaagcaaact gaggtggact gtgagtattt aaagagatgc tgcaacacat taccgatga
541 gaaccaaaga ctccggcaag aggttcaaga acttaaagca caaaaagtgt caccagcgtt
601 gtacatgcag ctgcccacga ccaccctcac cgtgtgtccg tcgtgtgaac agatcggaga
661 cacaaagtct gccacaagca aaaaccttg tactaaaaaa ccatctttt taacccctt
721 cactagttca tcggcagctt gttgataatt gattttatat gtggattatg ttgcataaaa
781 tttaaatcac tcatgcacag ccccacccctt ttttcagagt catgggctta tctagtggtg
841 gaagaaataa tgaaactgga atattgtaga aagatatcag aatacccact catattttt
901 tgtttttcta aagaatgtat tgttatttat tttgttgtgt aaattaattt cctgtttata
961 gtataacaag agaatatctt atttggatt
```

Fig. 12

SEQUENCE LISTING

```
<160> NUMBER OF SEQ ID NOS: 4

<210> SEQ ID NO 1
<211> LENGTH: 989
<212> TYPE: DNA
<213> ORGANISM: Helianthus annuus

<400> SEQUENCE: 1
taaacatcga tcaatctaca catcttttat tcagatggat tttcatggat ttgccgaaca      60
tgcactggaa ctacgcctta gtacaacatc atcggtggcc gaaaacacaa cgaatcccat     120
caagaagcct agcccgagtt ctgatcattg tcttgaacca tctctaactt tggctctttc     180
tggtgattca tgcggtggtt cgtcgttctc tatcgctagt gcgaagaggg aaagagaggt     240
tccgagtgaa gaatcggaga gaggaggaga gaacactagt ggtgaagaag atgaagatgg     300
tggtgtgaat ggtaagaaga aactcaggtt aactaaagct caatctggac tattagagga     360
agccttcaaa cttcacacaa ctttaaaccc taaacaaaag caagagcttg caagggactt     420
aaagctaagg cctagacaag ttgaagtatg gttccaaaac aggagagcaa gaacaaaact     480
gaagcaaact gaggtggact gtgagtattt aaagagatgc tgcaacacat taaccgatga     540
gaaccaaaga ctccggcaag aggttcaaga acttaaagca caaaaagtgt caccagcgtt     600
gtacatgcag ctgcccacga ccaccctcac cgtgtgtccg tcgtgtgaac agatcggaga     660
cacaaagtct gccacaagca aaaacccttg tactaaaaaa ccatcttttt ttaacccctt     720
cactagttca tcggcagctt gttgataatt gattttatat gtggattatg ttgcataaaa     780
tttaaatcac tcatgcacag ccccacccct ttttcagagt catgggctta tctagtggtg     840
gaagaaataa tgaaactgga atattgtaga aagatatcag aatacccact catatttttt     900
tgtttttcta aagaatgtat tgttatttat tttgttgtgt aaattaattt cctgtttata     960
gtataacaag agaatatctt atttggatt                                       989
```

```
<210> SEQ ID NO 2
<211> LENGTH: 9
<212> TYPE: DNA
<213> ORGANISM: Artificial Sequence
<220> FEATURE:
<223> OTHER INFORMATION: Hahb-10 transcription factor binding site
<220> FEATURE:
<221> NAME/KEY: misc_feature
<222> LOCATION: (5)..(5)
<223> OTHER INFORMATION: n can be C or G

<400> SEQUENCE: 2 caatnattg                                                                     9

<210> SEQ ID NO 3
<211> LENGTH: 17
<212> TYPE: DNA
<213> ORGANISM: Artificial Sequence
<220> FEATURE:
<223> OTHER INFORMATION: Synthetic hom5 oligonucleotide

<400> SEQUENCE: 3
cggtggttcg tcgttct                                                           17

<210> SEQ ID NO 4
<211> LENGTH: 26
<212> TYPE: DNA
<213> ORGANISM: Artificial Sequence
<220> FEATURE:
<223> OTHER INFORMATION: Synthetic 10cys oligonucleotide

<400> SEQUENCE: 4
ccgaattccc gatctgttca cacgac                                                 26
```

DNA CONSTRUCTS THAT CONTAIN *HELIANTHUS ANNUUS* HAHB-10 GENE CODING SEQUENCE, METHOD FOR GENERATING PLANTS WITH A SHORTENED LIFE CYCLE AND A HIGH TOLERANCE TO HERBICIDAL COMPOUNDS AND TRANSGENIC PLANTS WITH THAT SEQUENCE

BACKGROUND OF THE INVENTION

1. Field of the Invention

The present invention relates to the biotechnology field, more specifically to plant genetic engineering. The invention provides useful DNA sequences and constructs to obtain transgenic plants with a shorter life cycle and more tolerance to herbicides. More specifically, the invention provides new constructs that contain the sunflower Hahb-10 gene coding sequence, and a method to obtain plants with high tolerance to herbicides that produce oxidative stress, such as methyl viologen, and with a reduced life cycle in comparison to wild-type plants of the same species using these constructs.

2. Background Art

Homeobox Genes and their Participation in Plant Development

Plant development is determined by spatial and temporal gene expression programs. These programs are governed by regulatory proteins that act as transcription factors.

One distinctive characteristic of plants is that they can alter their development in response to environmental conditions in order to adapt to them. The first link in this response is a chain reaction triggered by a transcription factor that shoots biochemical and physiological changes in the plant. The knowledge of the transcription factors that drive these responses would be useful for the production of transgenic plants capable of adapting to unfavorable environmental conditions.

Transcription factors have specific DNA binding domains for particular sequences in the DNA promoter region in their target genes. The homeodomain is a 60-amino acid protein motif present in lots of eukaryotic transcription factors which are generally involved in the regulation of developmental processes. (Gehring, 1987). Homeodomains are present in almost every eukaryotic organism that has been investigated. Several homeobox genes have been isolated from fungi, animals and plants (Gehring et al., 1994).

In plants, several families of homeodomain proteins have been described (Chan et al., 1998). One of these families, named HD-Zip, comprises proteins with a typical leucine zipper motif adjacent to the C-terminal end of the homeodomain. As expected, these proteins bind DNA as dimers. The removal of the leucine zipper or the introduction of extra amino acids between the homeodomain and the leucine zipper significantly reduces binding affinity, indicating that the leucine zipper is responsible for the correct positioning of the homeodomain for efficient binding. The analysis of binding at different protein concentrations suggests that dimer formation is a prerequisite for DNA binding (Sessa et al., 1993; Palena et al., 1999).

It has been suggested, and subsequently supported by experimental evidence, that HD-Zip proteins are involved in regulating developmental processes associated with the response of plants to environmental conditions (Carabelli et al., 1993; Chan et al., 1998, Deng et al., 2002; Hanson et al., 2001; Himmelbach et al., 2002; Sawa et al., 2002; Schena et al., 1993; Soderman et al., 1999).

The expression of a member of *Arabidopsis* subfamily II, Athb-2/HAT4, is regulated by far-red light and its function is related to shade avoidance responses (Carabelli et al., 1993; Morelli and Ruberti, 2000; Morelli and Ruberti, 2002; Steindler et al., 1999). HAT2 is also a member of *Arabidopsis* subfamily II, and it has been characterized as an auxin inducible gene by DNA microarray screening (Sawa et al., 2002).

The isolation and characterization of several homeobox genes from sunflower has been previously reported (Chan and Gonzalez, 1994; Gonzalez and Chan, 1993; Gonzalez et al., 1997; Valle et al., 1997). Hahb-4 is a member of subfamily I and its function is related to water stress response (Dezar et al., 2005a; Dezar et al., 2005b; Gago et al., 2002).

Life Cycle of Plants

A plant's life cycle begins with seed germination and continues with seedling growth, until it constitutes a mature plant that flowers and produce fruits which contain seeds that will begin the plant cycle once again. Obtaining plants with shorter life cycles would be of major importance in modern agriculture.

Weeds and Herbicides

Weeds are unwanted plants that reduce both crop yield and quality by competing with the crop for water, nutrients and light. Weeds shade crops, take their water and nutrients, and make harvesting difficult.

It is well known that weeds might compete with the crop for nutrients, cause toxicity to livestock, might act as host for many different insects and plagues, interfere with the harvest task, and release several substances that could affect the normal development of crops of interest. This is why, for fanning activity, the weeds are seen as harmful and unwanted plants that should be eliminated from the countryside.

Several chemical substances, called herbicides, have been employed in the control of such weeds, causing their death or inhibiting their growth, without affecting the crop of interest. Paraquat is an herbicide in which the active ingredient is methyl viologen. This herbicide protects crops by controlling a wide range of annual and certain perennial weeds. Extensive use of Paraquat has resulted in weed resistance. In those cases where resistant biotypes have evolved, they have had no significant agricultural impact.

The active ingredient of Paraquat is methyl viologen, a redox cycler that produces specific reactive oxygen species, superoxide, in treated cells, generating a strong oxidative burst in sensitive plants. Superoxide generates cellular membrane weakening with subsequent ion imbalance, and the bleaching phenomenon in the sheets by the destruction of chlorophyll molecules.

The choice of treatment with herbicides varies according to the crop being cultivated. The quantities to use depend on the development stage of the plants and on the weed to be eliminated. Great efforts have been dedicated to the obtaining of species with good tolerance to herbicide treatment in order to apply those herbicides without damaging the crop of interest.

Different methodologies of vegetal improvement have contributed in this sense. However, we do not count the genotypes of all cultivable species that present resistance, given that neither classic cross-linking methods, nor molecular markers attend selection, or obtaining of mutants has been successful. Genetic engineering has contributed, in this sense, incorporating unique genes in the plants of interest generating resistance to the treatment with those compounds capable of eliminating weeds.

One of the main objectives of agro biotechnology is the identification of genes that generate plant resistance or tolerance to different herbicides to allow their use without detrimental effects on crops of interest.

BRIEF DESCRIPTION OF THE INVENTION

It is therefore an object of the invention to provide a gene sequence that encodes the transcription factor of *Helianthus annuus*, Hahb-10, or an active fragment, deletion or genetic variant of said gene. Said sequence is identified as SEQ ID NO:1 and derives from *Helianthus annuus* DNA, mRNA or cDNA. The Hahb-10 transcription factor binds to the DNA sequence 5'-CAAT(C/G)ATTG-3' (SEQ ID NO:2) in a DNA region, the promoter region, that regulates the transcription of several target genes involved in plant responses to changes in the environmental conditions.

It is another object of the present invention to provide vectors or DNA constructs that comprise a promoter sequence operable linked to the nucleic acid sequence SEQ NO:1, or a fragment, deletion or genetic variant thereof. Said vector will lead the expression of the transcription factor Hahb-10. This transcription factor will increase plant tolerance to herbicides such as Paraquat, which uses methyl viologen as its active ingredient, and will shorten the plant life cycle.

It is a further object of the present invention to provide a transgenic plant stably transformed with the nucleic acid sequence SEQ ID NO:1, or an active fragment, deletion or genetic variant thereof, wherein the sequence encodes Hahb-10 transcription factor, and wherein the plant is any plant including those of economical interest. The stably transformed plant is highly tolerant to herbicides that use oxidative burst as its functioning principle, i.e. methyl viologen, which is the active ingredient of Paraquat, and its life cycle is shorter when compared to their wild counterparts grown in the same conditions.

It is a further object of the present invention to provide a stably transformed seed containing the DNA sequence SEQ ID NO:1, or a fragment of given sequence, where the sequence encodes the transcription factor Hahb-10 or a fragment or variant thereof.

It is a further object of the present invention to provide a host cell stably transformed with the nucleic acid sequence of SEQ ID NO:1, or with an active fragment, deletion or genetic variant thereof, wherein the sequence encodes Hahb-10 transcription factor, and wherein the cell is a bacterium, a fungi, a plant or an animal cell. In a preferred embodiment the cell is a plant cell.

It is a further object of the present invention to provide a plant expression vector comprising a promoter region operably linked to the nucleic acid sequence of SEQ ID NO:1, or to a an active fragment, deletion or genetic variant of given sequence thereof, and a 3'UTR.

It is still another object of the invention to provide a method for obtaining a genetically modified plant resistant to herbicides and having a shorter life cycle, wherein the method comprises: designing and constructing a DNA molecule comprising a promoter region operably linked to a nucleic acid sequence encoding the transcription factor Hahb-10, or an active fragment, deletion or genetic variant thereof, and a 3'UTR, introducing said construct into a host cell, regenerating the transformed host cell to obtain a stably transformed complete plant expressing the transcription factor Hahb-10 and obtaining a crop that displays a shorter life cycle and/or a higher tolerance to herbicides as compared to wild-type plants. In a preferred embodiment, the promoter is the cauliflower mosaic virus 35S promoter.

It is another object of the invention to provide a method for producing a plant with a shorter life cycle when compared with a wild plant. This method includes the stable transformation of a cell or cell culture with the nucleic acid sequence of SEQ ID NO:1 or a fragment of given sequence, and the regeneration of an entire plant from this/these cell(s).

It is still another object of the invention to provide a plant expression cassette comprising: a) a promoter functional in plants, b) Hahb-10 coding sequence, or an active fragment, deletion or genetic variant thereof, and c) a 3'UTR linked 5'-3'.

It is a further object of the present invention to provide a transformed plant or its descendant, or seed, containing at least in one of its cells the Hahb-10 coding sequence, or an active fragment, deletion or genetic variant thereof, under the control of a plant functional promoter, wherein the plant is a monocot or a dicot plant, and belongs to some species of a group consisting of rice, maize, wheat, alfalfa, soybean, tobacco and/or cotton.

It is another object of the invention to provide a method for expressing at least one protein of interest in a host cell, comprising introducing the cassette into the host cell, and allowing the host cell to produce the protein of interest.

It is another object of the invention to provide a fragment, genetic variant or deletion of the DNA molecule comprising at least 100 consecutive bases with a homology of at least 80% to the sequence of cDNA between base pairs 1 and 989 of SEQ ID NO:1. In one embodiment, the DNA molecule comprises at least 150, 200, 250, 300, 350, 400, 450, 500, 550, 600, 650, 700, 750, or 800 consecutive bases with a homology of at least 80% to the sequence of cDNA between base pairs 1 and 989 of SEQ ID NO:1. In another embodiment, the DNA molecule comprises at least 100 consecutive bases with a homology of at least 85, 90, 95, 96, 97, 98, or 99% to the sequence of cDNA between base pairs 1 and 989 of SEQ ID NO:1.

The above and other objects, features and advantages of this invention will be better understood when taken in connection with the accompanying drawings and description.

BRIEF DESCRIPTION OF THE DRAWINGS/FIGURES

The present invention is illustrated by way of example in the following drawings wherein:

FIG. 1 shows that Hahb-10 is mainly expressed in mature leaves.

To perform expression analysis, we have used a specific probe that contains the 5' portion of Hahb-10. Northern blot analysis using this probe with total RNA extracted from different sunflower organs showed a high expression level in 30-day-old leaves and lower levels in seedlings, stems and cotyledons (FIG. 1). Lower but detectable levels of the transcript were observed in roots, carpels and fertile flowers. Quantitation of the signals indicated that expression in mature leaves is 4 to 5-fold the level of that found in seedlings. The results indicate that this transcription factor may have a function during vegetative/reproductive developmental states in photosynthetic tissues.

Total RNA samples (10 μg each) extracted from 4-day-old seedlings (1), 14-day-old stems (2), 14-day-old leaves (3), or 30-day-old leaves (4), carpels (5) or fertile flowers (6) were analyzed by electrophoresis, transferred onto nylon membranes and hybridized with a $^{32}$P-labeled Hahb-10 cDNA specific probe (upper panel). The same filter was hybridized with an rRNA probe as a control for RNA loading and transfer (lower panel). Spots obtained with the specific probe were quantified in reference to their rRNA using Image Pro Plus software. The graphic in the lower panel shows Hahb-10 transcript levels relative to the level in seedlings.

FIGS. 2A-2B show that Hahb-10 expression is strongly induced in etiolated seedlings.

2A: Total RNA samples (20 µg each) extracted from 4-day-old seedlings subjected to different treatments as described later were hybridized with a $^{32}$P-labeled Hahb-10 cDNA specific probe (A, upper panel). The same filter was hybridized with an rRNA probe as a control for RNA loading and transfer. Spots obtained with the specific probe were quantified in reference to their rRNA using Image Pro Plus software. The graphic shown in the lower panel shows Hahb-10 transcript levels relative to the level measured in heat shock treated seedlings. Quantitation of the signals has been done taking as standard value the signal obtained in these seedlings because the signal obtained in control seedlings was almost not detectable by the software used for this purpose.

2B: Total RNA samples (20 µg each) extracted from 7-day-old seedlings grown in normal illumination conditions (lane 1), in the dark (lane 2), or under continuous illumination at 40 cm from the light source applied to 4-day-old seedlings germinated in the dark during 3 additional days (lane 3) were analyzed by electrophoresis, transferred onto nylon membranes and hybridized with a $^{32}$P-labelled Hahb-10 cDNA specific probe (upper panel). The same filter was hybridized with an rRNA probe as a control for RNA loading and transfer (lower panel).

Figure 3:
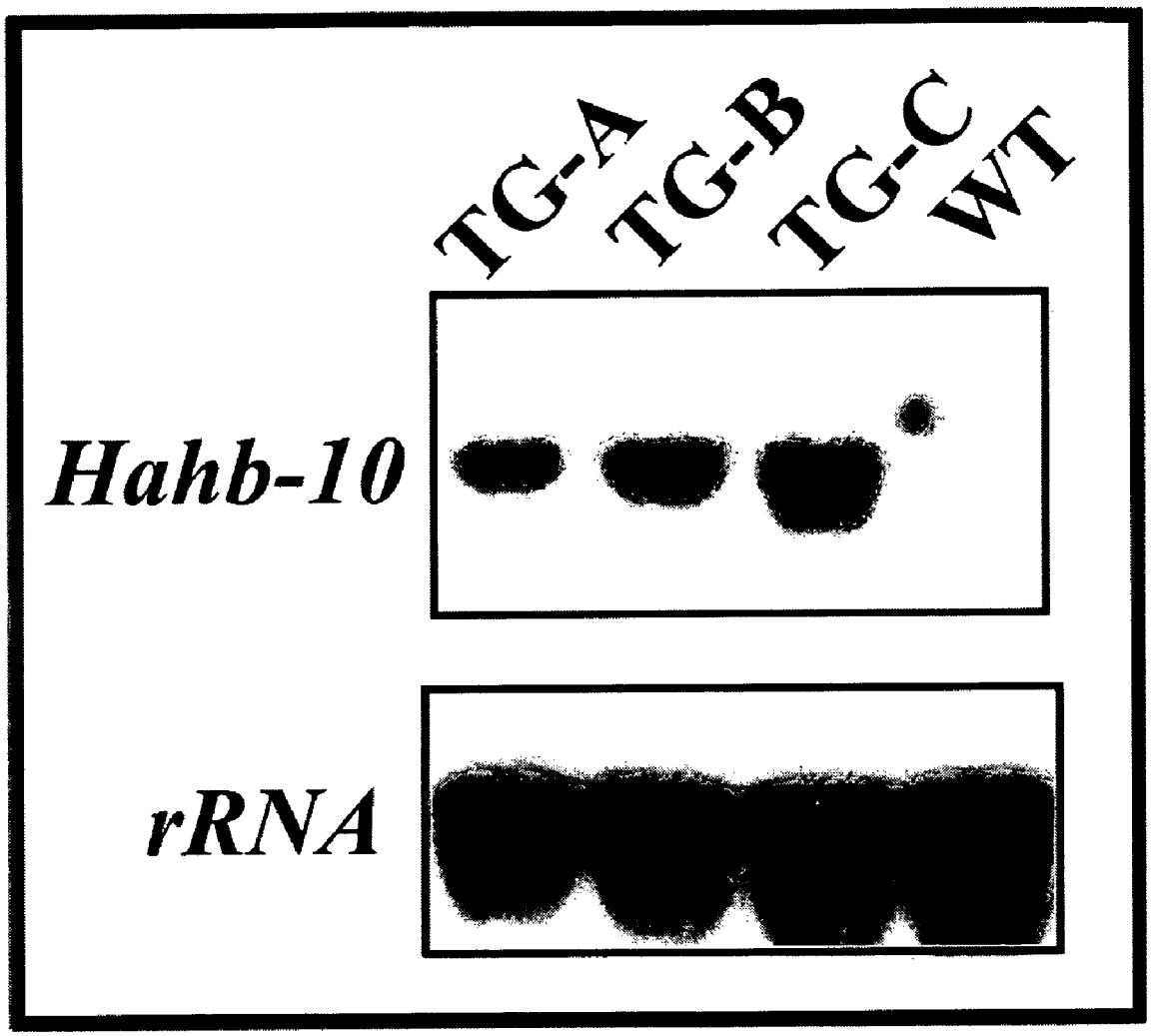

FIG. 3 shows the expression of sunflower Hahb-10 gene in *Arabidopsis* transgenic plants.

Northern blot analysis of transgenic *Arabidopsis* plants. Total RNA (10 µg) was extracted from wild-type (WT) and three independent transgenic plants (TG-A, B and C) overexpressing Hahb-10. Probes specific for Hahb-10 or rRNA were used as described above.

FIGS. 4A-4D show the phenotype of 35S:Hahb10 transgenic plants.

Comparison between transformed and control plants. 5A: top view of cotyledons; 5B: side view of cotyledons, 5C: 14-day-old-leaves; 5D: top view of 21-day-old plants of the four genotypes. (WT: wild-type plants; TG: transgenic plants from lines-A, -B, -C).

Figure 5:
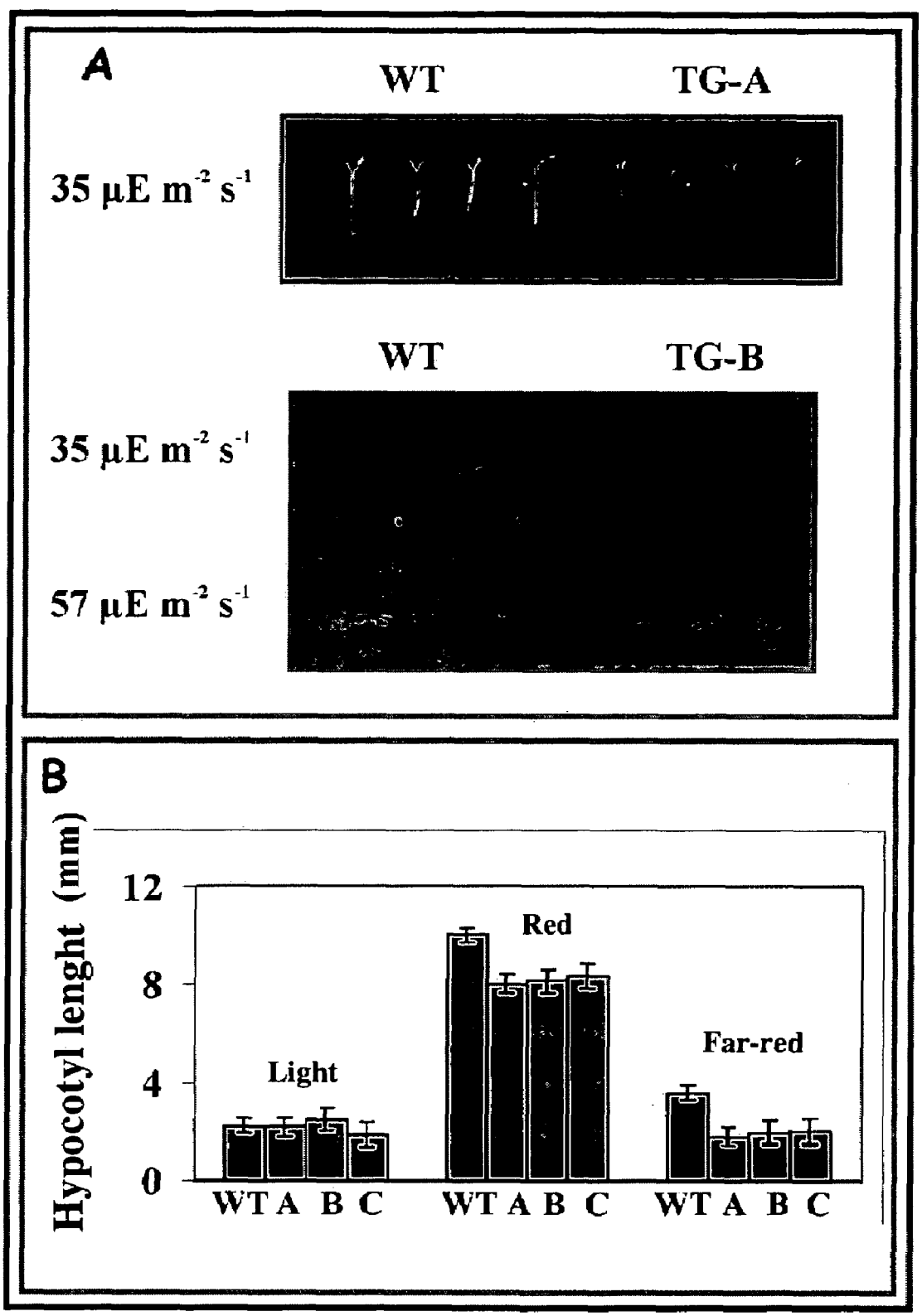

FIGS. 5A-5B shows that 35S:Hahb10 transgenic plants are less affected by changes in illumination intensity than their wild-type counterparts.

5A: Comparison between transformed and control 7-day-old seedlings grown at 35 µE m−2 s−1 (upper panel) and between 14-day-old plants grown at 57 µm−2 s−1 (lower panel).

5B: Hypocotyl length in 5-day-old seedlings grown on soil with different light qualities. This is a representative experiment done with 20 plants of each genotype. Hypocotyl length was measured with a ruler. Plants were grown in normal illumination conditions or subjected to red enriched light or far-red enriched light. Controls were done with normal illumination as described later. (WT: wild-type plants; TG-A, -B and -C: three independent over expressing Hahb-10 transgenic lines).

FIGS. 6A-6B shows that 35S:Hahb10 transgenic plants develop faster than non-transformed ones.

6A: comparison of developmental state between transformed and control 21-day-old plants grown on soil (four plants per 8 cm diameter pot).

6B: difference in the developmental state between transgenic and non transformed plants in a typical experiment done with twenty plants per 8 cm diameter pot.

Figure 7:
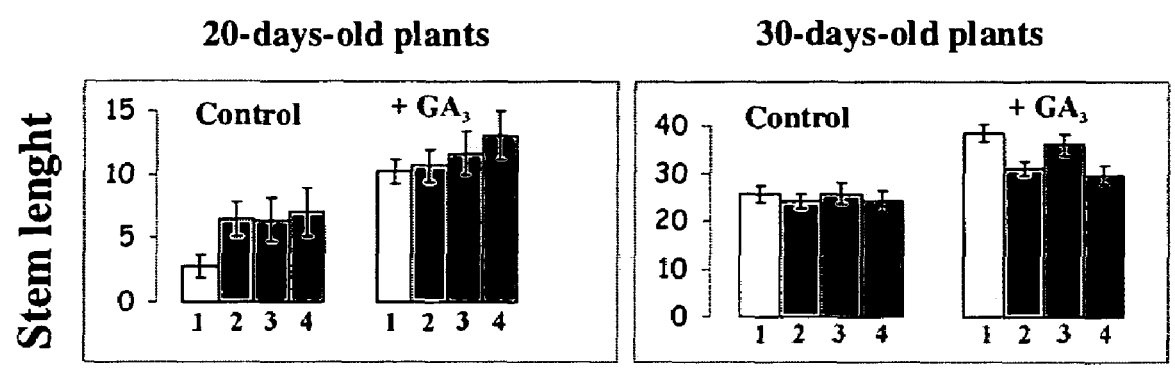

FIG. 7 shows that stem elongation is almost unaffected in gibberellin treated transgenic plants.

Stem height was measured with a ruler in non transformed (1) or 35S-Hahb10 transgenic plants (2: line A; 3: line B and 4: line C). Grey bars represent three transgenic lines and white bars represent wild-type plants. Right series in each panel represent GA3 treated plants while left series represent their non-treated counterparts. The first panel represents the observed results in 20-day-old plants while the second panel shows the results observed after a second hormone treatment in 30-day-old plants.

Figure 8:
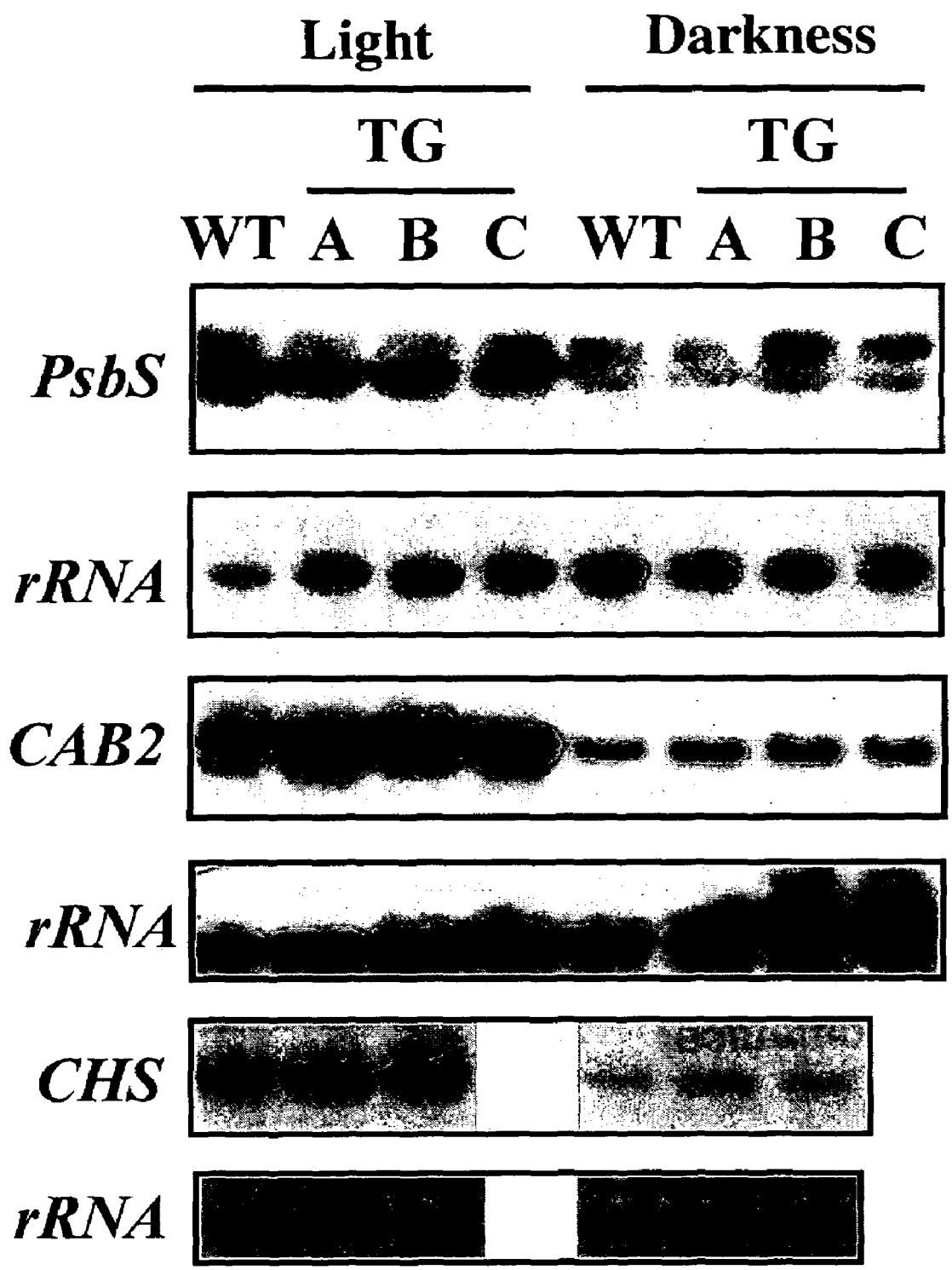

FIG. 8 shows that the expression of the PsbS gene is reduced in Hahb-10 overexpressing transgenic plants.

For Northern blot analysis of non-transformed and transgenic *Arabidopsis* plants, total RNA (10 µg) was extracted from 4-day-old seedlings of wild-type (WT) or transgenic plants overexpressing Hahb-10 grown under normal illumination conditions or subjected to 8 h of darkness as described later. Probes specific for PsbS, CAB2, CHS or rRNA were used.

FIGS. 9A-9E shows the effect of the herbicide Paraquat 2 days after application. (WT: wild-type plants; TG-A, -B and -C: three independent overexpressing Hahb-10 transgenic lines).

9A: control plants were grown in normal conditions for 30 days.

9B: plants treated with 10 µM methyl viologen.

9C: plants treated with 20 µM methyl viologen.

9D: plants treated with 30 µM methyl viologen.

9E: upper view of 21-day-old transgenic and wild-type plants treated with 10 µM methyl viologen.

Figure 10:
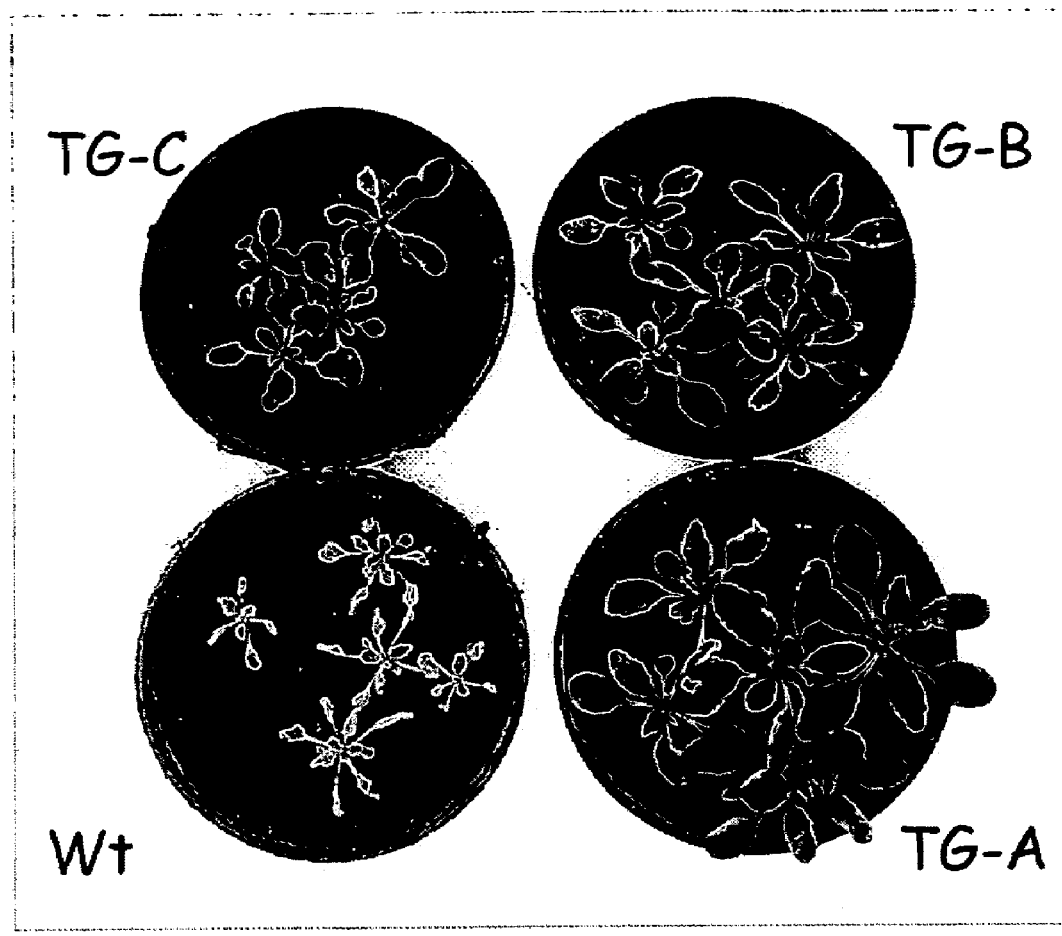

FIG. 10 shows that Hahb-10 transgenic plants are less susceptible to methyl viologen than their wild-type counterparts. Plants were treated with 10 µM methyl viologen and observed 48 h later. (WT: wild-type plants; TG-A, -B and -C: Hahb-10 transgenic lines).

Figure 11:
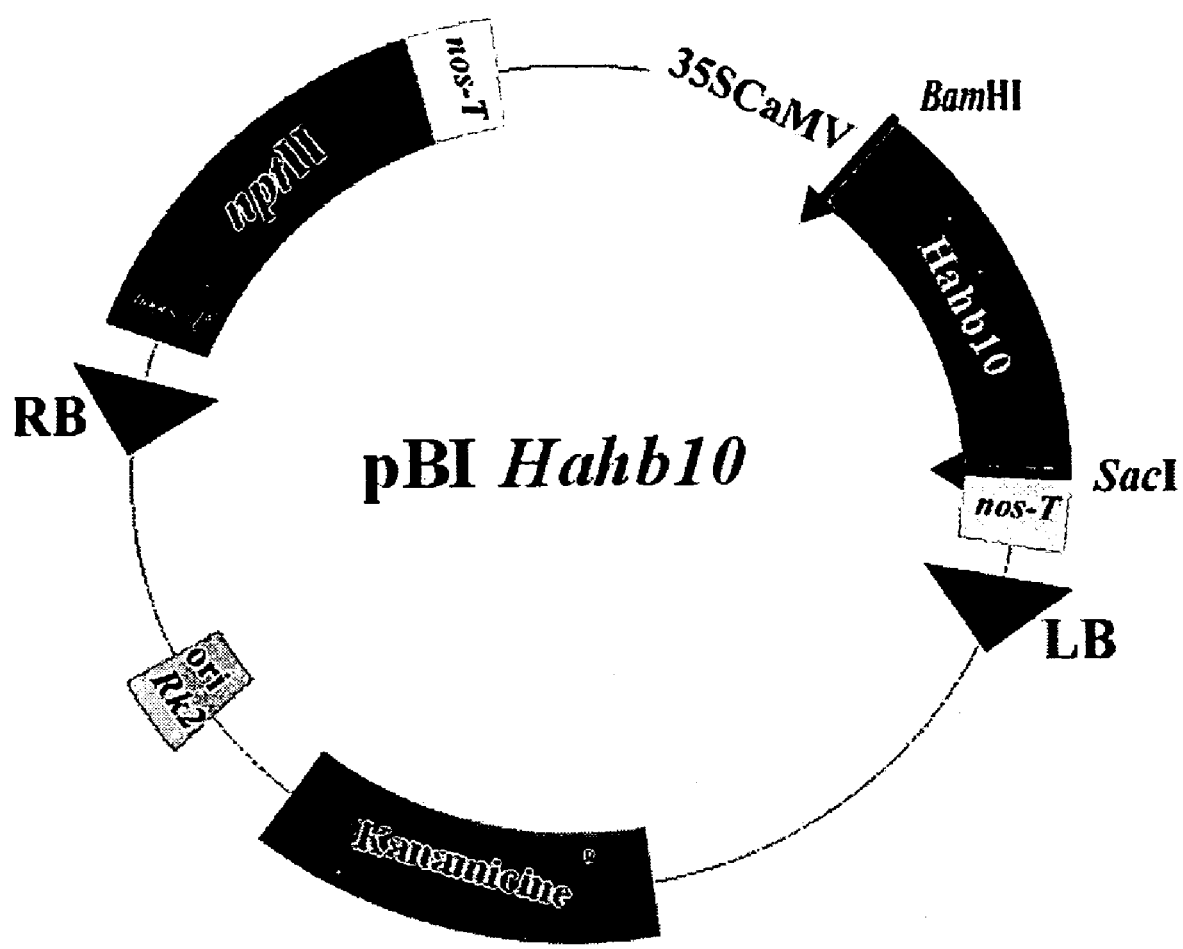

FIG. 11 shows the pBI-Hahb-10 expression vector map used in the present invention, which comprises Kanamicin R: Kanamycin resistance gene.

nos-P: nopaline synthase gene promoter.

nos-T: nopaline synthase gene terminator.

Hahb-10: sunflower Hahb-10 gene coding sequence.

LB: left end.

RB: right end.

CaMV35S: cauliflower mosaic virus 35S promoter.

Ori RK2: prokaryotic origin of replication.

SacI: SacI restriction site.

BamHI: BamHI restriction site.

FIG. 12 shows the Hahb-10 nucleotide sequence used in the constructs.

The sequence expressed in the construct corresponds to bases 35 to 745 of SEQ ID NO:1. The start and stop codon are indicated.

DETAILED DESCRIPTION OF THE INVENTION

Now referring in detail to the invention, this one comprises DNA constructs containing the sunflower Hahb-10 gene coding sequence, and transgenic plants transformed with these constructs, in order to obtain plants with a shorter life cycle and more resistance to herbicides producing oxidative stress, such as methyl viologen, both characteristics of agronomical value.

The term "fragment," as used herein, refers to a polynucleotide comprising any portion of consecutive bases of the sequence of SEQ ID NO:1, wherein the fragment encodes a polypeptide that retains at least 10% (e.g., at least 20, 30, 40, 50, 60, 70, 80, or 90%) of the activity of the full-length Hahb-10 polypeptide.

The term "deletion," as used herein, refers to a polynucleotide comprising any portion of the sequence of SEQ ID NO:1, wherein the deletion encodes a polypeptide that retains at least 10% (e.g., at least 20, 30, 40, 50, 60, 70, 80, or 90%) of the activity of the full-length Hahb-10 polypeptide. The term deletion includes one or more internal deletions of the sequence of SEQ ID NO:1 as well as truncations of the 5' and/or 3' ends of the sequence of SEQ ID NO:1.

The term "genetic variant," as used herein, refers to a polynucleotide comprising a nucleotide sequence that is at least 80% identical (e.g., at least 85, 90, 95, 96, 97, 98, or 99% identical) to the sequence of SEQ ID NO:1, wherein the genetic variant encodes a polypeptide that retains at least 10% (e.g., at least 20, 30, 40, 50, 60, 70, 80, or 90%) of the activity of the full-length Hahb-10 polypeptide.

Sequence identity is calculated by comparing two optimally aligned sequences over that region of comparison, determining the number of positions at which the identical nucleotide occurs in both sequences to yield the number of matched positions, dividing the number of matched positions by the total number of positions in the region of comparison (i.e., the window size), and multiplying the result by 100 to yield the percentage of sequence identity. In one aspect, percent identity is calculated as the percentage of nucleotides in the smaller of two sequences which align with an identical nucleotide in the sequence being compared, when four gaps in a length of 100 nucleotides may be introduced to maximize alignment (Dayhoff, in Atlas of Protein Sequence and Structure, Vol. 5, p. 124, National Biochemical Research Foundation, Washington, D.C. (1972), incorporated herein by reference). A determination of identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which in incorporated herein by reference in its entirety).

The term "activity," as used herein in reference to fragments, deletions, and genetic variants of Hahb-10, refers to the biological activity of Hahb-10 (e.g., the ability to shorten the life cycle of a plant or increase herbicide resistance in a plant) and/or the functional activity of Hahb-10 (e.g., the ability of the polypeptide to recognize and bind to a specific DNA sequence such as the sequence 5'-CAAT(C/G)ATTG-3' (SEQ ID NO:2). Biological activity can be measured by any method known in the art, including the methods disclosed herein. Functional activity can be measured by routine methods known in the art for measurement of transcription factor activity, including methods disclosed in Sambrook et al. (1989).

For the present invention, we performed expression and functional studies on a member of the sunflower HD-Zip II subfamily, Hahb-10. Previously described experimental results suggest that redox conditions may operate to regulate the activity of this and other members of this subfamily (Tron et al., 2002). The studies performed in the present invention indicate that Hahb-10 is mainly expressed in mature leaves and other photosynthetic tissues. Moreover its expression is up-regulated by etiolation and gibberellins. We have observed that *Arabidopsis* plants overexpressing Hahb-10 have a characteristic phenotype that affects leaf shape, form and color, growth rate and life cycle under standard growth conditions. Additionally, transgene overexpression in plants provides them tolerance to the herbicide methyl viologen. Furthermore, transgenic plants showed altered responses to changes in illumination conditions compared with wild-type plants. We propose that the product of this gene might be involved in light-dependent responses related to plant development.

HD-Zip proteins, unique to plants, are proposed as good candidates to trigger developmental responses to changes in environmental conditions, a characteristic feature of plants. Several authors have found that expression of some members of the HD-Zip family of transcription factors is regulated by different external factors like illumination or water stress (Carabelli et al., 1993; Carabelli et al., 1996; Chan et al., 1998; Gago et al., 2002; Lee and Chun, 1998; Schena and Davis, 1992; Schena et al., 1993; Söderman et al., 1994; Söderman et al., 1996; Söderman et al., 1999).

Transgenic plants bearing constructs that alter the expression of HAT4/Athb2 (a well studied member of the *Arabidopsis* Hd-Zip II subfamily) exhibit changes in morphology and developmental rate (Carabelli et al., 1993; Schena et al., 1993). Plants expressing a HAT4/Athb-2 antisense construct are shorter and develop slower than normal, whereas those expressing a HAT4/Athb-2 sense construct are taller and develop faster than wild-type. Schena et al. concluded that HAT4/Athb-2 functions as a key regulator of developmental rate. These observations are reminiscent of those based on the effect of luminous environmental stimulus.

HAT2, another member of the HD-Zip II subfamily, was characterized as an early auxin-inducible gene in seedlings by DNA microarray screening (Sawa et al., 2002). HAT2 overexpressing plants produce long hypocotyls, epinastic cotyledons, long petioles and small leaves, which are typical characteristics of some auxin-overproducing mutants (Delarue et al., 1998). These plants show reduced auxin sensitivity when compared with wild-type ones. On the other hand, these transgenic plants showed reduced lateral root elongation. These observations led Sawa et al. (2002) to suggest that HAT2 plays opposite roles in the shoot and root tissues, thus regulating auxin-mediated morphogenesis.

Hahb-10 has been shown to encode an HD-Zip transcription factor that belongs to the sunflower HD-Zip II subfamily (Gonzalez et al., 1997; Tron et al., 2002). Induction of Hahb-10 expression in etiolated seedlings suggests that it may have a potential role in signaling illumination conditions. To address this question, we used an overexpression strategy by choosing *Arabidopsis* as a model system and transforming those plants with constructs capable of leading Hahb-10 gene expression. The expression levels of Hahb-10 in the 35S: Hahb10 transgenic lines used in our study are higher than their *Arabidopsis* counterparts under control conditions and its own expression level in sunflower.

Flowering in transgenic plants occurs earlier than in non transformed ones. Flower formation is a complex morphological event and is attained when plants reach a certain age or size. An important group of plants, that includes *Arabidopsis*, requires appropriate environmental conditions to develop flowers. Light and temperature are two factors that profoundly affect flowering time. It seems that Hahb-10 somehow influences signal transduction pathways involved in flowering. Additional experiments should be performed to elucidate the mechanisms involved. The experimental observations made with the Hahb-10 gene resemble in part those made with the Athb-2/HAT4 gene by Schena. Similarities include the induction of both genes in dark-adapted plants, and the high steady-state transcript levels detected in the vegetative phase of plant growth. Plants that overexpress either of these genes are darker green than wild-type ones, have smaller roots, less expanded cotyledons, and in both, life cycle is shortened, because of the early flowering time. On the other hand, some clear differences exist between both transgenes: HAT4/Athb2 increases its transcript levels in flowering plants while Hahb-10 does not; far-red illumination strongly induces expression of the Arabidopsis gene while induction of the sunflower gene is rather low. Overexpression of HAT4/Athb2 results in a defect in germination in dark conditions while the sunflower gene causes the opposite effect, i.e. Hahb-10 overexpressing plants germinate faster than wild-type ones and became healthier either after long periods of etiolation. In addition, HAT4/Athb2 overexpressing plants present longer hypocotyls while Hahb-10 transgenic plants present shorter ones with respect to non transformed plants (Schena et al., 1993; Steindler et al., 1999). These observations lead us to conclude that these genes are not orthologues and that they have different functions.

Athb-2/HAT4 has been described as a negative regulator of paralogous genes. It recognizes its own promoter region and its endogenous expression is repressed in overexpressing transgenic plants (Ohgishi et al., 2001; Steindler et al., 1999). Once again, the observations in Hahb-10 transgenic plants can not be explained as a product of the repression of Arabidopsis homologous genes. Indeed, HAT4/Athb2 and HAT22 transcript levels do not change in Hahb-10 overexpressing plants.

Gibberellins are a group of hormones involved in a wide variety of developmental processes including stem elongation and various aspects of seed germination. In reproductive development, gibberellins can affect the transition from the juvenile to the mature stage, as well as floral initiation, sex determination and fruit set. In the present study it could be observed that GA3 induces Hahb-10 expression in sunflower and that overexpressing plants show some characteristics of plants that have been treated with gibberellins. This fact allows us to speculate that Hahb-10 may be a positive regulator of gibberellin biosynthesis and/or function. This conclusion is basically based on three observations: major seed germination in darkness conditions, accelerated transition from juvenile to the adult phase and earlier floral initiation, all together those observations result in a shorter life cycle of the plant. These phenomena are affected by gibberellins and are also observed in Hahb-10 overexpressing plants that have not been treated with gibberellins. The behavior of the Hahb-10 gene when plants are treated with gibberellins resembles that of the Arabidopsis HAT2 gene when plants are treated with auxins. In both cases HD-Zip gene expression is induced by the hormones and overexpressing plants are almost insensitive to treatment with them. Both cases suggest that the genes are involved in these developmental processes and that they are mediated by hormones.

Phytochromes are photochromatic proteins that regulate the responses to light quality, quantity and time of exposure. In Arabidopsis, there are five genes that encode phytochromes PHYA-E. Phytochromes A and B are involved in the regulation of flowering time in an antagonist way (Ma et al., 2001). Transgenic plants overexpressing PHYA display an early flowering time compared to their non-transformed counterparts (Bagnall et al., 1995). Phytochrome B is a photoreceptor involved in detecting red to far-red light ratios associated with plant density. Transgenic plants that ectopically express the Arabidopsis PHYB gene increase tuber yield in field-grown transgenic potato crops (Casal et al., 2004). It has been reported that this effect is larger at very high densities of sowing (Boccalandro et al., 2003). We have described that the acceleration in development observed in Hahb-10 overexpressing plants is also more pronounced at high densities. It is possible that the sunflower gene is also implicated in a PHYA and PHYB-induced signal transduction pathway.

A good number of genes are regulated by phytochromes, constituting the molecular basis for the phytochrome-developmental changes under far red/red light (Ma et al., 2001). Regarding the effects produced in Hahb-10 expression in sunflower and the behavior of plants overexpressing this gene, we decided to analyze the levels of some of the expressed genes that are induced by light. We have examined the transcript levels of three light inducible genes (CAB, PsbS and CHS) and found a strongly decreased transcript level in far-red light expression of PsbS in transgenic plants with respect to non transformed ones. This finding may indicate that Hahb-10 directly or indirectly regulates PsbS expression, especially under far-red illumination conditions. The other two genes did not show a distinct behavior between wild and transgenic plants, indicating that their regulation would be induced by other pathways. Using a very different strategy, other authors also suggested different regulatory mechanisms for these light-inducible genes (Dae-Shik et al., 2003).

For many years, big efforts have been made concerning tolerance to different stress types and reducing plant life cycle. In this sense, positive results would allow a better profit of the cultivable soil and could be of important economical impact in world wide agriculture. However, success has been limited by the complexity of responses that involve morphologic, physiologic, biochemical and genetic processes. A better understanding of the function that the proteins codified by these genes play in adaptation to different environmental conditions, would provide the basis to generate effective strategies to produce better adapted plants. Results from the present invention suggest that obtaining a Hahb-10 transgenic plant would allow one to obtain a plant with a shorter life cycle, more tolerant to herbicides and capable of growing at high densities.

In the present invention, we analyzed the effects of the sunflower transcription factor Hahb-10 overexpression in transgenic Arabidopsis thaliana. This gene was selected because it belongs to the HD-Zip II subfamily.

Transgenic Arabidopsis thaliana plants overexpressing Hahb-10 under the 35S cauliflower mosaic virus promoter show special phenotypic characteristics like darker cotyledons and planar leaves, and a pronounced acceleration in development, shortening life cycle about 25%, due to a shortened flowering time. When the number of plants per pot was increased, the difference in developmental rate between transgenic and non transformed individuals was increased.

To develop the present invention, Helianthus annuus L. (sunflower cv. contiflor 15, from Zeneca) seeds were surface sterilized and grown on filter paper inside Petri dishes for 4 days in the dark or under different illumination conditions as described in the figure legends. Seedlings were then transferred to plastic supports containing soil and were grown for variable times depending on the purpose of the experiment.

Water stress was imposed by transferring 7-day-old seedlings from humid Petri dishes to Petri dishes with dry filter paper.

Cold shock was imposed by transferring 7-day-old seedlings grown in humid Petri dishes to a cold chamber maintained at 4° C. for 4 hours.

Heat shock was imposed in a similar way, but transferring plants to a 45° C. regulated incubator for 1 hour.

Hormone treatments were carried out by transferring 7-day-old seedlings to Petri dishes with fresh MS medium/Gamborg vitamins supplemented with either 200 μM gibberellin (gibberellic acid, GA3 for plant tissue culture, Sigma), 10 μM ABA or sprayed with Ethrel®, an ethylene releasing agent (2-chloroethylphosphoric acid).

Treatments with the herbicide Paraquat were carried out by growing transgenic and wild-type 21-day-old plants under normal conditions and spraying them with methyl viologen at concentrations of 10, 20 or 30 μM.

*Arabidopsis thaliana* Heyhn. ecotype Columbia seeds (Col-0) were purchased from Lehle Seeds (Tucson, Ariz.). Plants were grown on soil in a growth chamber at 22-24° C. under long-day photoperiods (16 h of illumination by a mixture of cool-white and GroLux fluorescent lamps) at an intensity of 200 $\mu m^{-2} s^{-1}$. Plants used for the different treatments or for transformation were grown in 8 cm diameter×7 cm height pots during the time indicated in the figures.

Transformed *Agrobacterium tumefaciens* strain GV2260 was used to obtain transgenic *Arabidopsis* plants by the floral dip procedure (Clough and Bent, 1998). Transformed plants were selected on the basis of kanamycin resistance and positive PCR, carried out on genomic DNA with the specific oligonucleotides hom5 (5'-CggTggTTCgTCgTTCT-3') (SEQ ID NO:3) and 10cys (5'-CCgAATTCCCgATCTgT-TCACACgAC-3') (SEQ ID NO:4).

To assess Hahb-10 expression, Northern blot analysis was performed on T2 transformants. Three positive independent lines (arising from two different transformation experiments) were further reproduced and homozygous T3 and T4 plants were used to analyze the expression levels of Hahb-10 and the phenotype of transgenic plants. Plants transformed with pBI101.3 or pBI121 were used as controls.

*Arabidopsis* transgenic or wild-type plants were grown under normal illumination conditions for 15 days. After this, the plants were sprayed with 200 μM GA3. This treatment was repeated at day 25. Stem length was measured in 20- and 30-day-old plants with a ruler.

Total RNA from sunflower or from *Arabidopsis* were isolated and prepared as described by Almoguera and Jordano (1992) or Carpenter and Simon (1998), respectively. For Northern analysis, RNA was denatured with formaldehyde, separated in a 1.5% (w/v) agarose/6% formaldehyde gel, and blotted onto nylon membranes (Hybond N, Amersham-Pharmacia) essentially as described by Sambrook et al. (1989). Hybridization was performed overnight at 65° C. in 6×SSC (1×SSC is 0.15 M NaCl, 0.015 M Na$_3$-citrate, pH 7.0), 0.1% (w/v) polyvinylpyrrolidone, 0.1% (w/v) BSA, 0.1% (w/v) Ficoll, 0.5% (w/v) SDS. An EcoRI/SpeI fragment (from +1 to +275), corresponding to the 5'-non coding region of the Hahb-10 cDNA plus the first 241 nucleotides of the coding region, which does not include the Hd-Zip domain, was labeled with [$^{32}$P]dATP ($1\times10^8$ dpm/μg) by random priming (Sambrook et al., 1989) and used as probe. Filters were autoradiographed using Bio-Max films and transcreen (Kodak) overnight. To check the amount of total RNA loaded and transferred in each lane, filters were then re-probed with a 25S rRNA from *Vicia faba* under similar conditions as those described above, except that hybridization was performed at 62° C.

Probes for the PsbS, CAB2 and CHS genes were obtained from clones APZ10g10, APZ49a09 and RZ115f04, respectively, kindly provided by the Kazusa DNA Research Institute (Japan).

EXAMPLES

Example 1

Hahb-10 is Primarily Expressed in Mature Leaves

To perform expression analysis, we have used a specific probe that contains the 5' portion of Hahb-10. Northern blot analysis using this probe with total RNA extracted from different sunflower organs showed a high expression level in 30-day-old leaves and lower levels in younger leaves and stem (FIG. 1). Still lower, but clearly detectable levels of the transcript were observed in seedlings, carpels, and fertile and sterile flowers (not shown). Quantitation of the signals indicated that expression in mature leaves is 10-fold higher than the level of that found in carpels, the plant organ where Hahb-10 transcript levels are lowest, but still detectable.

The results indicate that this transcription factor may have a function during vegetative developmental states in photosynthetic tissues.

Example 2

Hahb-10 Expression is Regulated by Light

Since Hahb-10 belongs to the HD-Zip family, and members of this family are supposed to be involved in developmental processes regulated by external factors and/or hormones, we have investigated this possibility by subjecting sunflower plants to different treatments. Northern blot analysis was carried out using total RNA samples (20 μg each) extracted from 4-day-old seedlings subjected to different treatments as described above. Samples were electrophoresed, transferred onto nylon membranes and hybridized with a $^{32}$P-labeled Hahb-10 cDNA specific probe (A, upper panel). The same filter was hybridized with an rRNA probe as a control for RNA loading and transfer. Spots obtained with the specific probe were quantified in reference to their rRNA using Image Pro Plus software. The graphic shown in the lower panel shows Hahb-10 transcript levels relative to the level measured in heat shock treated seedlings. FIG. 2A shows the effect of such treatments on Hahb-10 transcript levels.

Figure 2:
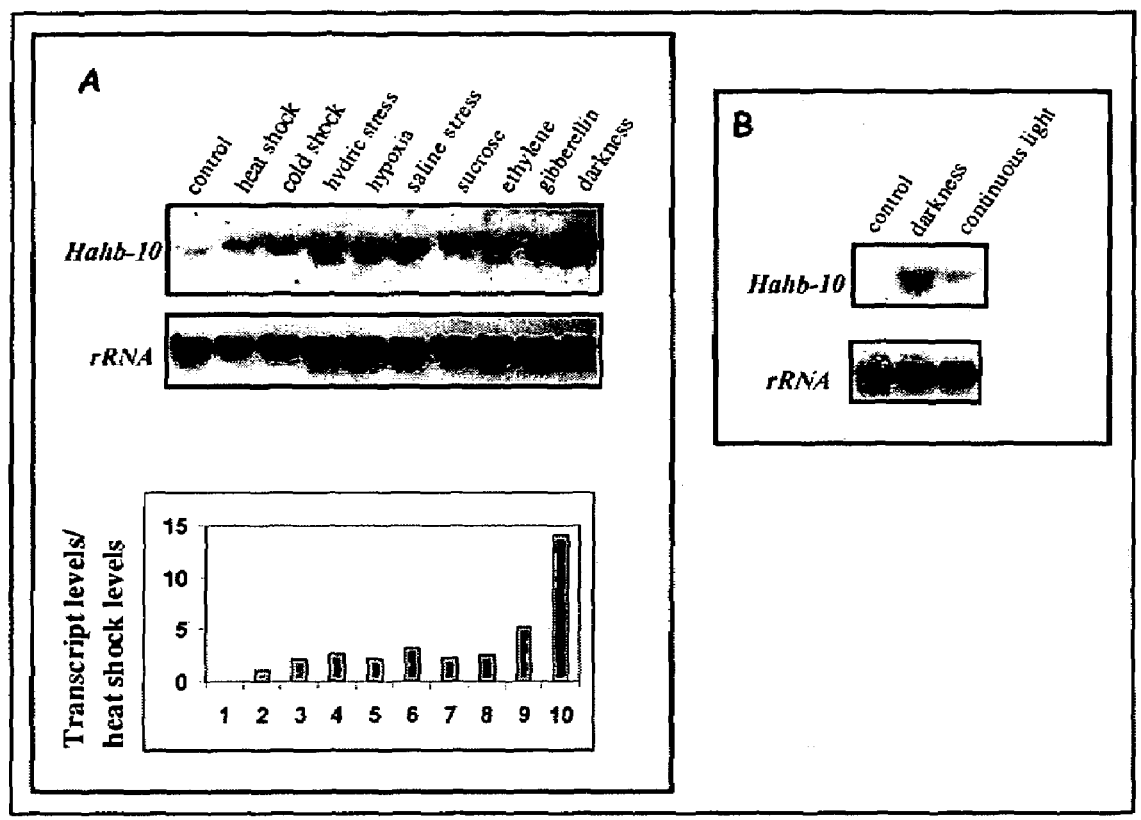

Heat or cold shock, water stress and hypoxia slightly enhanced Hahb-10 mRNA levels (FIG. 2). Addition of sucrose (10% w/v) or 30 mM ethrel produced a similar effect, while 100 μM gibberellic acids raised Hahb-10 transcript levels 5-fold with respect to the heat-shock treatment. The strongest induction (14-fold) was observed when plants were grown in the dark for 7 days, indicating that the expression of this gene may be regulated by illumination conditions.

Example 3

The Most Important Effect in the Induction of Hahb-10 Expression is Produced by Dark In order to investigate this point, sunflower plants were subjected to different illumination conditions: continuous light at different distances from the illumination source or in the dark. FIG. 2B shows that Hahb-10 expression is high in the dark, and extremely low under continuous illumination.

Changes in illumination intensity did not affect Hahb-10 expression in 25-day-old leaves (data not shown).

Example 4

Obtaining *Arabidopsis* Lines Overexpressing Hahb-10

To investigate the in vivo function of Hahb-10, we have used an overexpression approach. The coding region of Hahb-10 was fused to the 35S promoter of Cauliflower mosaic virus, and the construct was used to transform *Arabidopsis* plants. Several homozygous lines were recovered and, after preliminary analysis, three transgenic independent lines, named 35S:Hahb10-A, -B and -C, were selected for more detailed analysis. FIG. 3 shows a Northern blot hybridized with the 5' region of Hahb-10 that does not include the HD-Zip domain coding region, where total RNA from non transformed or transgenic plants was analyzed. The probe did not hybridize with RNA extracted from wild-type plants, indicating the absence of cross-reactions with members of the *Arabidopsis* HD-Zip family or with other genes. Signals of variable strength were observed with RNA from the different transgenic plants suggesting that they express Hahb-10 mRNA at different levels. We have also tested if *Arabidopsis* homologues of this gene change their expression level in transgenic plants. Neither HAT22 nor Athb-2/HAT4 transcript levels were affected by the presence of the transgene (data not shown).

Example 5

Phenotype of Hahb-10 Overexpression Lines

Figure 4:
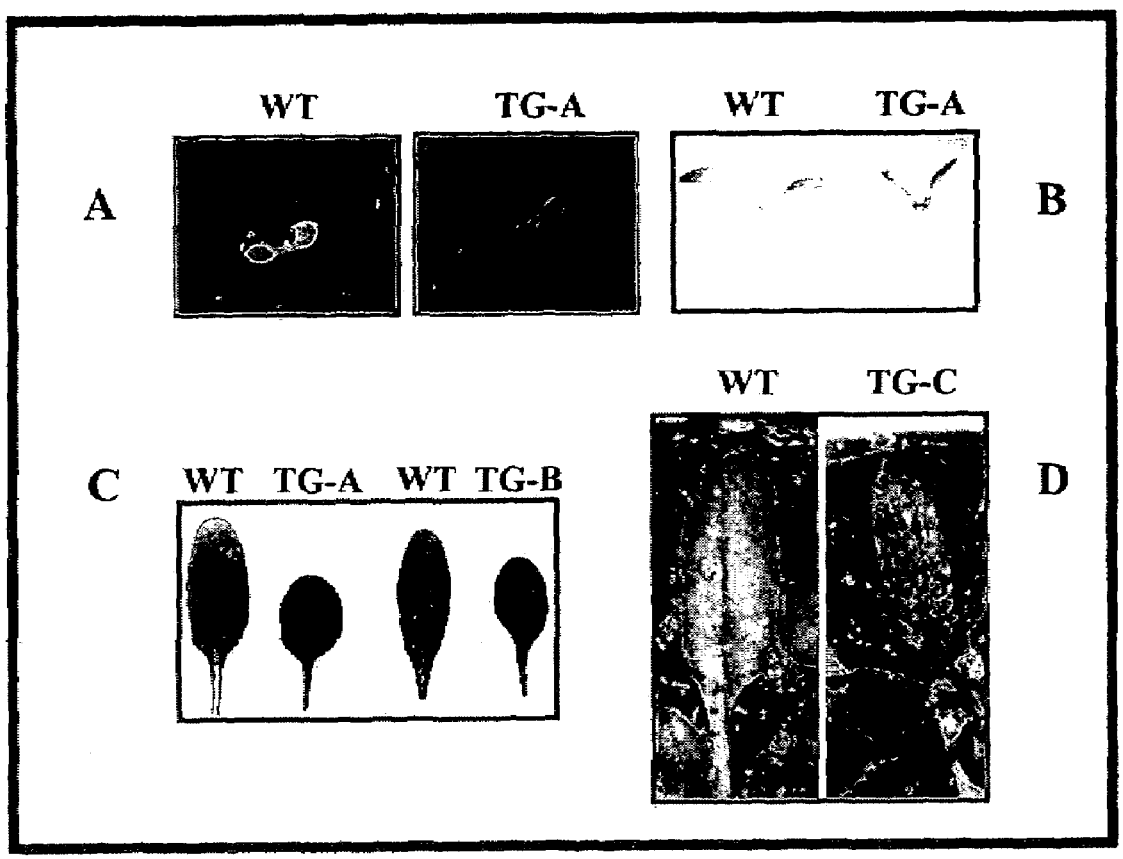

Compared with wild-type plants, 35S-Hahb10 transgenic plants exhibited a characteristic phenotype when cultured under standard conditions. When grown on soil, root length is shorter than in their wild-type counterparts (Table I), cotyledons were less expanded and remained at a smaller angle with respect to the hypocotyl axis, while in non transformed plants, as expected, cotyledons were positioned perpendicular to the hypocotyl (FIGS. 4A and 4B). In addition, all photosynthetic tissues presented a darker green color. Leaves were smaller and planar in the transgenic lines compared with those of the non transformed plants (FIGS. 4C and 4D). *Arabidopsis thaliana* transgenic plants that express Hahb-10 under the 35S cauliflower mosaic virus promoter show special phenotypic characteristics as darker cotyledons and planar leaves, and a pronounced acceleration of development reducing the plant life cycle by 25% due to a shortened flowering time.

TABLE I

Roots are shorter in transgenic than in non-transformed plants

| Root Length | Wild-Type Plants | Transgenic Plant Line A | Transgenic Plant Line B | Transgenic Plant Line C |
|---|---|---|---|---|
| Average and standard deviation (mm) | 17.7 ± 2.9 | 14.8 ± 1.8 | 13.7 ± 2.2 | 12.7 ± 2.2 |

Root length in 8-day-old Hahb-10 overexpressing (TG line A, B, C) or non transformed plants grown on Petri dishes under normal conditions was measured with a ruler. This is a representative experiment done with 20 plants of each genotype. Root length is expressed in mm.

Example 6

Photosynthetic Tissues of Transgenic Plants Present a Darker Green Color than those of Wild-type Counterparts As shown in Table II, pigment content is higher in transgenic plants than in wild-type plants. Chlorophylls a and b as well as Anthocyanin display increased values relative to mg of tissue in 35S:Hahb10 plants in comparison to wild-type ones.

TABLE II

Pigment content is higher in transgenic plants than in wild-type plants

| Pigment | WT | TG-A | TG-B | TG-C |
|---|---|---|---|---|
| Chlorophyll a | 71.6 ± 1.1 | 79.8 ± 1.1 | 84.9 ± 1.5 | 88.0 ± 1.5 |
| Chlorophyll b | 27.6 ± 1.3 | 38.0 ± 1.4 | 40.2 ± 1.4 | 42.1 ± 1.4 |
| Anthocyanin | 0.06 ± 0.01 | 0.14 ± 0.02 | 0.15 ± 0.02 | 0.22 ± 0.02 |

Pigments were quantified as described previously. Values are expressed as μg of each pigment in 100 mg of tissue. This is a representative experiment done with 20 plants of each genotype.

Example 7

Effect of Illumination Conditions in Transgenic *Arabidopsis* Plants

The phenotype of Hahb-10 overexpression lines suggests that they may have altered developmental responses to light. In order to investigate this, we have grown transgenic plants at different distances from the light source or under complete darkness in pots intercalated in the same tray with non transformed plants (FIGS. 5A and B). As can be observed, in the dark (upper panel of FIG. 5A) transgenic plants show a defect in hypocotyl elongation. Hypocotyl elongation is a typical response observable in etiolated wild-type plants. In a similar way, a decrease in light intensity did not affect transgenic plant development (FIG. 5A, lower panel), while wild type plants showed elongated hypocotyls under these conditions. Under red enriched light or far-red enriched light transgenic plants show reduced hypocotyl elongation compared with wild-type plants (FIG. 5B).

These results indicate that Hahb-10 overexpression lines are less sensitive to changes in light conditions.

Example 8

Figure 6:
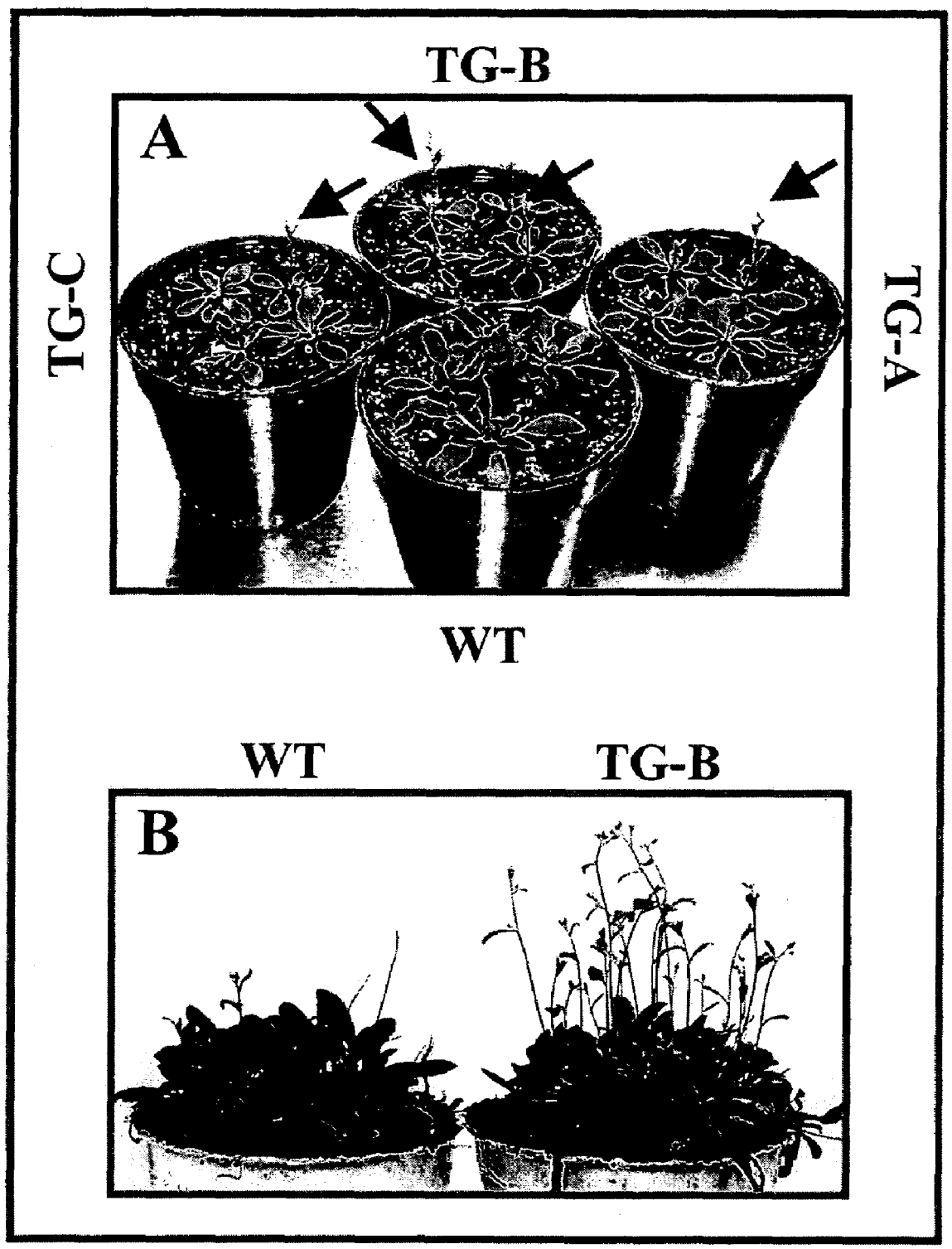

Transgenic *Arabidopsis* Plants Show a Shorter Life Cycle Compared with Wild-Type Plants Transgenic plants showed a faster stem elongation rate than wild-type ones (FIG. 6). Flowering also occurs earlier in transgenic plants. The differences in height between wild-type and transgenic plants became less evident upon progression of the reproductive stage of development. Seed maturation begun approximately 50 days after germination in transgenic plants while under the same conditions wild-type plants started this process approximately 65 days after germination.

Table III illustrates experiments performed with the three independent Hahb-10 overexpression lines and wild-type plants grown under normal conditions. Plant height was greater in all transgenic lines until 35 days after germination. This difference disappeared at day 45, showing both plant types had the same height but not the same maturation grade. Transgenic plants matured earlier than non-transformed ones and seeds could be collected 1-2 weeks in advance. Seed production was similar in transgenic and non-transformed plants. Several experiments have been performed where the total weight of dried seeds produced by plants of both genotypes was measured. The observed difference in weight is smaller than the standard deviation calculated in each experiment performed with 12 individuals of each genotype.

Otherwise, transgenic plants are more tolerant to prolonged incubation in the dark. Table IV shows the percentage of surviving plants after 5 days of darkness. While in the non-transformed group only 18% of the plants survived, the transgenic group showed an average of 75% survivors.

Significant differences were observed between experiments performed with either two five or twenty plants per pot. When the number of plants per pot increased, the difference in developmental rate between transgenic and non-transformed individuals increased proportionally, i.e. under space and/or nutrient limiting conditions, Hahb-10 overexpressing plants were less affected than non-transformed ones (FIG. 7, lower panel).

TABLE III

Hahb-10 transgenic plants show a faster stem elongation and have a shorter life cycle compared with wild-type plants

| Plants age (days) | Wild-Type Plants | Transgenic Plant Line A | Transgenic Plant Line B | Transgenic Plant Line C |
|---|---|---|---|---|
| 28 | 13.82 ± 1.01 | 19.45 ± 1.71 | 18.32 ± 3.1 | 18.44 ± 1.05 |
| 35 | 27.00 ± 3.79 | 30.00 ± 1.17 | 31.06 ± 2.75 | 28.76 ± 1.79 |
| 45 | 31.20 ± 2.00 | 31.62 ± 1.04 | 32.67 ± 1.60 | 29.2 ± 1.28 |

Stem height of Hahb-10 expressing transgenic and non transformed *Arabidopsis* plants was measured with a ruler at different times after sowing. This is a representative experiment performed with twenty plants of each genotype. Stem length is expressed in mm.

TABLE IV

Hahb-10 overexpressing transgenic plants cope with long periods of dark

| Days after etiolation | Wild-Type Plants | Transgenic Plant Line A | Transgenic Plant Line B | Transgenic Plant Line C |
|---|---|---|---|---|
| 2 | 81 | 70 | 70 | 95 |
| 3 | 39 | 79 | 77 | 85 |
| 5 | 18 | 69 | 72 | 80 |
| Control | 90 | 80 | 75 | 98 |

Plants were put in the culture chamber in absolute darkness during different periods. After the etiolation treatments, they were transferred to normal illumination conditions for ten days. Healthy plants were counted 4 days after the transfer. The percentage of survivors after etiolation during the periods indicated is shown.

Example 9

Effect of Gibberellins on Hahb-10 Overexpressing Plants

Among the hormones tested as effectors of Hahb-10 expression, gibberellins proved to be positive regulators. In order to investigate the response of Hahb-10 overexpressing lines to this hormone, we treated plants with 200 µM gibberellins as described above. As can be observed in FIG. 7, non-transformed plants showed a 3.7-fold increase in stem elongation with respect to their non-treated controls 5 days after the treatment, while transgenic stem length increased only 1.6-fold. After the second treatment, a similar result was observed; i.e. transgenic plants are almost insensitive to the hormone treatment (1.2-fold induction on average) compared with wild-type plants (1.5 fold induction on average), indicating that Hahb-10 overexpressing plants show characteristics of gibberellin treated non transformed plants.

Example 10

Possible Target Genes of Hahb-10

Since Hahb-10 belongs to the sunflower HD-Zip family, we tested the expression levels of *Arabidopsis* homologues, Athb-2/HAT4 and HAT22, in transgenic and wild-type plants. As deduced from Northern blot experiments, neither Athb-2/HAT4 nor HAT22 transcript levels were significantly affected (not shown). This result enhances the conclusion that Hahb-10 overexpression is directly responsible for the phenotype observed.

In order to investigate the mechanism of action of Hahb-10, we have also analyzed the expression levels of several genes that are regulated by illumination conditions (Dae-Shilk et al., 2003). We have prepared probes for PsbS (At1g44575), CAB2 (At1g29920) and CHS (At5g13930), encoding a photosystem II associated protein, a chlorophyll a/b binding protein and chalcone synthase, respectively, to investigate this point. Notably, steady-state transcript levels of PsbS, showed significant changes in Hahb-10 overexpressing plants with respect to control plants, especially under far-red illumination (FIG. 8). This gene diminishes its expression level 5-fold under far-red illumination in transgenic plants compared to its expression level under normal illumination conditions, whereas only a 1.5-fold reduction was observed in non transformed plants under the same conditions. At the same time, the expression level in transgenic plants under normal illumination conditions was slightly lower than in their non-transformed counterparts. Since the in vitro sequence bound by Hahb-10 is not present in the PsbS promoter region (3000 bp upstream of the transcription initiation 16 site), PsbS may be an indirect target gene of transcription factor Hahb-10. Hahb-10 may affect signal transduction pathway(s) that are involved in regulating the response of PsbS to different light conditions.

Example 11

Hahb-10 Overexpressing Plants are More Tolerant to the Herbicide Paraquat (Methyl Viologen) than Wild-Type Ones In order to study the effect of Hahb-10 overexpression on the tolerance to herbicides, transgenic and wild-type 21-day-old *Arabidopsis thaliana* were grown under normal conditions and were sprayed with methyl viologen at concentrations of 10, 20 or 30 µM. Once sprayed, they were left at the same illumination and temperature conditions for 24 hours and, at that time, leaf impairment was easily observable. One week after MV treatment, chlorophyll content in the leaves from both genotypes was analyzed. Plants were allowed to recover for three days and the percentage of survivors, either wild-type or transgenic ones expressing the Hahb-10 gene, was recorded.

Figure 9:
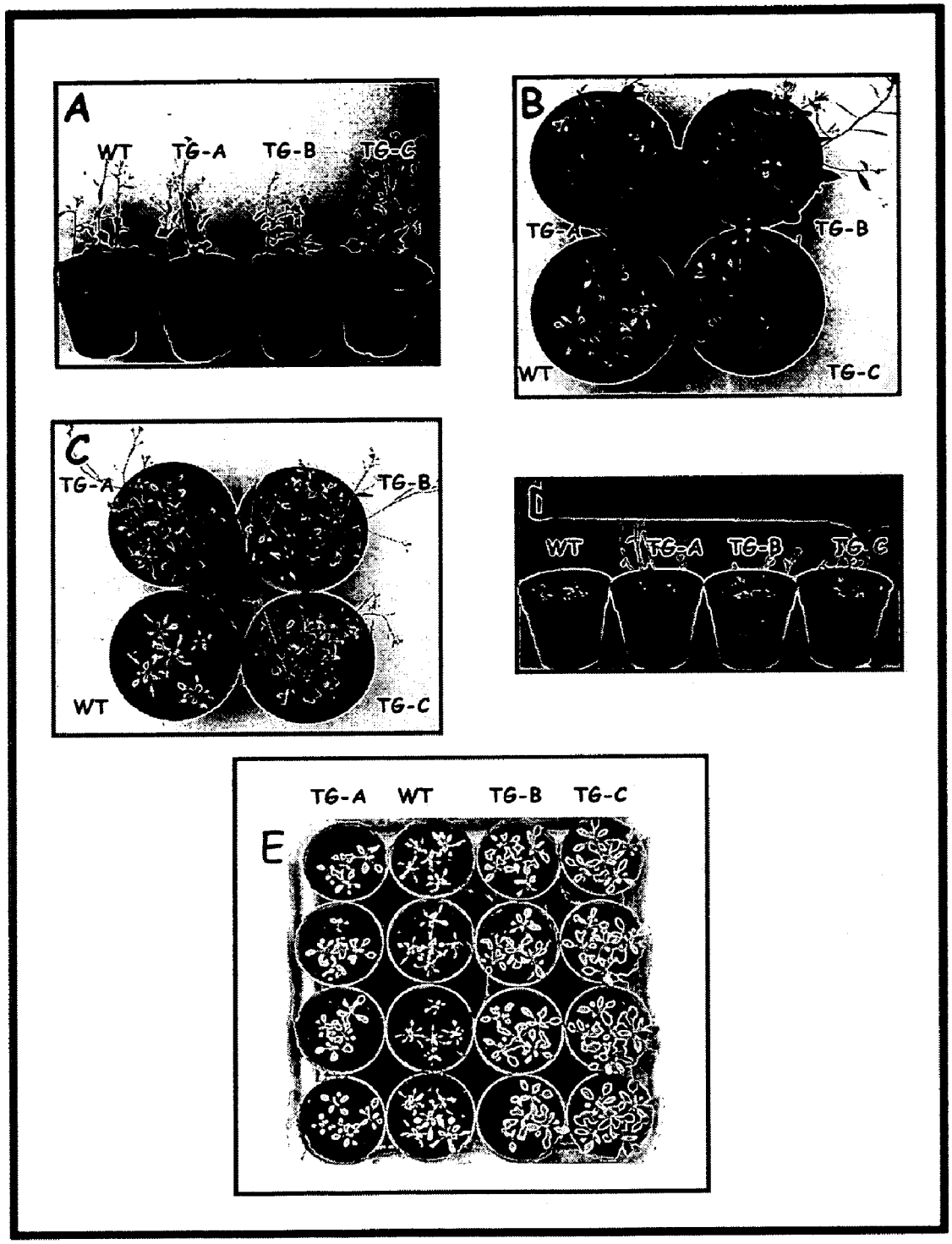

Transgenic plants from three independent lines coming from different transformation events were shown to be resistant to the herbicide methyl viologen at concentrations between 10 and 30 µM in a dose-dependent manner (FIGS. 9 and 10). In comparison, non-transformed counterparts were dramatically affected by the same treatment, correlating to the methyl viologen concentration used.

REFERENCES

Almoguera, C. and Jordano, J. 1992. Developmental end environmental concurrent expression of sunflower dry-seed-stored low-molecular-weight heat-shock protein and Lea mRNAs. Plant Mol. Biol. 19: 781-792.

Bagnall D J, King R W, Whitelam G C, Boylan M T, Wagner D, Quail P H. 1995. Flowering responses to altered expression of phytochrome in mutants and transgenic lines of *Arabidopsis thaliana* (L.) Heynh. Plant Physiol. 108:1495-503.

Boccalandro, H. E., Ploschuk, E. L., Yanovsky, M. J., Sanchez, R. A., Gatz, C. A. and Casal, J. J. 2003. Increased phytochrome B alleviates density effects on tuber yield of field potato crops. Plant Physiol. 133:1539-46.

Carabelli, M., Morelli, G., Whitelam, G. and Ruberti, I. 1996. Twilight-zone and canopy shade induction of the Athb-2 homeobox gene in green plants. Proc. Natl. Acad. Sci. USA 93: 3530-3535.

Carabelli, M., Sessa, G., Baima, S., Morelli, G. and Ruberti, I. 1993. The *Arabidopsis* Athb-2 and -4 genes are strongly induced by far-red-rich light. Plant J. 4:469-479.

Carpenter, C. D. and Simon, A. E. 1998. Preparation of RNA. In Methods in Molecular Biology, vol. 82: *Arabidopsis* Protocols (eds. J. Martinez-Zapater and J. Salinas), pp. 85-89. Humana Press Inc., Totowa, N.J., USA.

Casal, J. J., Fankhauser, C., Coupland, G. and Blazquez, M. A. 2004. Signalling for developmental plasticity. Trends Plant Sci. 9: 309-14.

Chan, R. L., Gago, G. M., Palena, C. M. and Gonzalez, D. H. 1998. Homeoboxes in plant development. Biochim. Biophys. Acta 1442: 1-19.

Chan, R. L. and Gonzalez, D. H. 1994. A cDNA encoding an HD-Zip protein from sunflower. Plant Physiol. 106: 1687-1688.

Clough, S. J. and Bent, A. F. 1998. Floral dip: a simplified method for *Agrobacterium*-mediated transformation of *Arabidopsis thaliana*. Plant J. 16:735-743.

Dae-Shilk, C., Sung-Hyun, H., Hong-Gil, N. and Moon-Soo, S. 2003. FIN5 Positively regulates far-red light responses in *Arabidopsis thaliana*. Plant Cell Physiol. 44: 565-572.

Delarue, M., Prinsen, E., Onckelen, H. V., Caboche, M. and Bellini, C. 1998. Sur2 mutations of *Arabidopsis thaliana* define a new locus involved in the control of auxin homeostasis. Plant J. 14: 603-611.

Deng, X., Phillips, J., Meijer, A. H., Salamini, F. and Bartels, D. 2002. Characterization of five novel dehydration-responsive homeodomain leucine zipper genes from the resurrection plant *Craterostigma plantagineum*. Plant Mol. Biol. 49:601-610.

Dezar C A, Gago G M, Gonzalez D H, Chan R L. 2005. Hahb-4, a sunflower homeobox-leucine zipper gene, is a developmental regulator and confers drought tolerance to *Arabidopsis thaliana* plants. Transgenic Res. 14:429-440.

Gehring, W. J., Affolter, M., Bürglin, T. 1994. Homeodomain proteins. Annu. Rev. Biochem. 63: 487-526.

Gehring, W. J. 1987. Homeo boxes in the study of development. Science 236:1245-1252.

Gonzalez, D. H. and Chan R. L. 1993. Screening cDNA libraries by PCR using lambda sequencing primers and degenerate oligonucleotides. Trends Genet. 9: 231-232.

Gonzalez, D. H., Valle, E. M., Gago, G. M. and Chan, R. L. 1997. Interaction between proteins containing homeodomains associated to leucine zippers from sunflower. Biochim. Biophys. Acta 1351: 137-149.

Hanson, J., Johannesson, H. and Engstrom, P. 2001. Sugar-dependent alterations in cotyledon and leaf development in transgenic plants expressing the HD Zip gene ATHB13. Plant Mol. Biol. 45: 247-262.

Himmelbach, A., Hoffmann, T., Leube, M., Hohener, B. and Grill, E. 2002. Homeodomain protein ATHB6 is a target of the protein phosphatase ABI1 and regulates hormone responses in *Arabidopsis*. EMBO J. 21: 3029-3038.

Lee, Y. H. and Chun, J. Y. 1998. A new homeodomain-leucine zipper gene from *Arabidopsis thaliana* induced by water stress and abscisic acid treatment. Plant Mol. Biol. 37: 377-384.

Ma, L., Li, J., Qu, L., Hager, J., Chen, Z., Zhao, H. and Deng, X. W. 2001. Light control of *Arabidopsis* development entails coordinated regulation of genome expression and cellular pathways. Plant Cell 13: 2589-2607.

Mattsson, J., Söderman, E., Svenson, M., Borkird, C. and Engström, P. 1992. A new homeobox-leucine zipper gene from *Arabidopsis thaliana*. Plant Mol. Biol. 18:1019-1022.

Morelli, G. and Ruberti, I. 2000. Shade avoidance responses. Driving auxin along lateral routes. Plant Physiol. 122: 621-626.

Morelli, G. and Ruberti, I. 2002. Light and shade in the photocontrol of *Arabidopsis* growth. Trends Plant Sci. 7: 399-404.

Ohgishi, M., Oka, A., Morelli, G., Ruberti, I. and Aoyama, T. 2001. Negative autoregulation of the Arabidopsis homeobox gene ATHB-2. Plant J. 25: 389-398.

Palena, C. M., Gonzalez, D. H. and Chan, R. L. 1999. A monomer-dimer equilibrium modulates the interaction of the sunflower homeodomain leucine-zipper protein Hahb-4 with DNA. Biochem. J. 341: 81-87.

Ruberti, I., Sessa, G., Lucchetti, S. and Morelli, G. 1991. A novel class of proteins containing a homeodomain with a closely linked leucine zipper motif. EMBO J. 10: 1787-1791.

Sambrook, J., Fritsch, E. F. and, Maniatis, T. 1989. Molecular Cloning: A Laboratory Manual, 2nd ed., Cold Spring Harbor Laboratory Press, Cold Spring Harbor, N.Y.

Sawa, S., Ohgishi, M., Goda, H., Higuchi, K., Shimada, Y., Yoshida, S. and Koshiba, T. 2002. The HAT2 gene, a member of the HD-Zip gene family, isolated as an auxin inducible gene by DNA microarray screening, affects auxin response in *Arabidopsis*. Plant J. 32: 1011-1022.

Schena, M. and Davis, R. W. 1992. HD-Zip protein members of *Arabidopsis* homeodomain protein superfamily. Proc. Natl. Acad. Sci. USA 89:3894-3898.

Schena, M., Lloyd, A. M. and Davis, R. W. 1993. The HAT4 gene of *Arabidopsis* encodes a developmental regulator. Genes Dev. 7: 367-379.

Sessa, G., Morelli, G. and Ruberti, I. 1993. The Athb-1 and -2 HD-Zip domains homodimerize forming complexes of different DNA binding specificities. EMBO J. 12: 3507-3517.

Söderman, E., Hjellstrom, M., Fahleson, J. and Engstrom, P. 1999. The HD-Zip gene ATHB6 in *Arabidopsis* is expressed in developing leaves, roots and carpels and up-regulated by water deficit conditions. Plant Mol. Biol. 40: 1073-1083.

Söderman, E., Mattsson, J. and Engström, P. 1996. The *Arabidopsis* homeobox gene ATHB-7 is induced by water deficit and by abscisic acid. Plant J. 10: 375-381.

Söderman, E., Mattsson, J., Svenson, M., Borkird, C. and Engström, P. 1994. Expression patterns of novel genes encoding homeodomain leucine-zipper proteins in *Arabidopsis thaliana*. Plant Mol. Biol. 26: 145-154.

Steindler, C., Carabelli, M., Borello, U., Morelli, G. and Ruberti, I. 1997. Phytochrome A, phytochrome B and other phytocrome (s) regulate ATHB-2 gene expression in etiolated and green *Arabidopsis* plants. Plant, Cell Environ. 20: 759-763.

Steindler, C., Matteucci, A., Sessa, G., Weimar, T., Ohgishi, M., Aoyama, T., Morelli, G. and Ruberti, I. 1999. Shade avoidance responses are mediated by the ATHB-2 HD-zip protein, a negative regulator of gene expression. Development 126:4235-4245.

Taiz, L. and Zeiger, E. 1998. Plant Physiology, 2nd edition (Sinauer Associates, Inc., Publishers, Sunderland, Mass.) chapter 20.

Tron A E, Bertoncini C W, Chan R L, Gonzalez D H. 2002. Redox regulation of plant homeodomain transcription factors. J Biol. Chem. 2002 277(38):34800-034807.

Valle, E. M., Gonzalez, D. H., Gago, G. and Chan, R. L. 1997. Isolation and expression pattern of hahr1, a homeobox-containing cDNA from *Helianthus annuus*. Gene 196: 61-68.

Wang, Y., Henriksson, E., Söderman, E., Nordin Henriksson, K., Sundberg, E. and Engström, P. 2003. The *Arabidopsis* homeobox gene, ATHB16, regulates leaf development and the sensitivity to photoperiod in *Arabidopsis*" Dev. Biol. 264: 228-239.

---

What is claimed is:

1. A method for obtaining a genetically modified plant having a shorter life cycle and a high tolerance to herbicides, the method comprising:
   (a) providing a DNA construct comprising a promoter operably linked to nucleotides 35 to 745 of SEQ ID NO:1 which encodes the transcription factor Hahb-10,
   (b) introducing said construct into a host cell to produce a transformed host cell, and
   (c) regenerating the transformed host cell to obtain a stably transformed complete plant expressing the transcription factor Hahb-10 and displaying a shorter life cycle and a higher tolerance to herbicides as compared to wild-type plants.

2. The method of claim 1, wherein the DNA construct further comprises a 3'UTR.

3. The method of claim 2, wherein the promoter is the cauliflower mosaic virus 35S promoter.

4. The method of claim 1, wherein said herbicides produce oxidative stress.

5. The method of claim 4, wherein the herbicide is methyl viologen.

* * * * *